(12) United States Patent
Adarraga

(10) Patent No.: US 8,171,570 B2
(45) Date of Patent: *May 8, 2012

(54) EXOSKELETON

(75) Inventor: Juan Moran Adarraga, Tarragona (ES)

(73) Assignee: Golden Crab S.L., Madrid (ES)

( * ) Notice: Subject to any disclaimer, the term of this patent is extended or adjusted under 35 U.S.C. 154(b) by 1056 days.

This patent is subject to a terminal disclaimer.

(21) Appl. No.: 12/103,196

(22) Filed: Apr. 15, 2008

(65) Prior Publication Data

US 2008/0294080 A1   Nov. 27, 2008

Related U.S. Application Data

(63) Continuation of application No. PCT/ES2008/000243, filed on Apr. 14, 2008.

(60) Provisional application No. 61/035,918, filed on Mar. 12, 2008, provisional application No. 61/035,924, filed on Mar. 12, 2008, provisional application No. 60/907,914, filed on Apr. 23, 2007, provisional application No. 60/907,913, filed on Apr. 23, 2007.

(51) Int. Cl.
    *A41D 13/00*   (2006.01)

(52) U.S. Cl. .............................................. 2/22

(58) Field of Classification Search ............. 2/16, 22, 2/24, 62, 911; 128/882, 108.1; 602/26, 62; 280/611

See application file for complete search history.

(56) References Cited

U.S. PATENT DOCUMENTS

| | | | |
|---|---|---|---|
| 2,803,467 A | 8/1957 | von Opel | |
| 3,614,119 A | 10/1971 | Wilkes | |
| 3,826,509 A | 7/1974 | Smolka | |
| 3,909,028 A | 9/1975 | Courvoisier et al. | |
| 3,928,872 A | 12/1975 | Johnson | |
| 3,947,051 A | 3/1976 | Sittmann | |
| 4,136,404 A | 1/1979 | Lange | |
| 4,408,600 A | 10/1983 | Davis | |
| 4,420,895 A | 12/1983 | Baumann et al. | |
| 4,568,296 A | 2/1986 | Newell | |

(Continued)

FOREIGN PATENT DOCUMENTS

CN   1593861 A   3/2005

(Continued)

OTHER PUBLICATIONS

Umetami, Y. et al., "'Skil Mate', Wearable Exoskeleton Robot" 1999 IEEE International Conference on Systems, Man, and Cybernetics, 1999. IEEE SMC '99 Conference Proceedings 1999 0-7803-5731-0/99.

(Continued)

*Primary Examiner* — Tejash Patel

(74) *Attorney, Agent, or Firm* — Sughrue Mion, PLLC

(57) ABSTRACT

Exoskeleton for physical activity, specially snow skiing, for preventing knee, leg and hip injuries by preventing the excessive torsion of the knee and other movements that could be dangerous for the person wearing it. The exoskeleton diverts the potential dangerous forces to the strong parts of the body and resists the generated forces when it reaches dangerous anatomical positions. The exoskeleton includes at least one first support member configured to couple above the knee; at least one second support member configured to couple below the knee; both of them linked together by a linkage assembly that limits that the coupling to the body of the support members reach dangerous positions; and at least one angle limitation mechanism that limits the relative rotation between the first support member and the second support member.

43 Claims, 23 Drawing Sheets

U.S. PATENT DOCUMENTS

| | | | |
|---|---|---|---|
| 4,617,920 | A | 10/1986 | Carsalade |
| 4,776,326 | A | 10/1988 | Young et al. |
| 4,872,665 | A | 10/1989 | Chareire |
| 4,967,734 | A | 11/1990 | Rennex |
| 5,011,136 | A | 4/1991 | Rennex |
| 5,016,869 | A | 5/1991 | Dick et al. |
| 5,295,704 | A * | 3/1994 | Flock ............................ 280/611 |
| 5,362,288 | A | 11/1994 | Razon |
| 5,376,139 | A | 12/1994 | Pitkin |
| 5,405,408 | A | 4/1995 | Pitkin |
| 5,845,540 | A | 12/1998 | Rosheim |
| 5,961,541 | A | 10/1999 | Ferrati |
| 5,980,435 | A * | 11/1999 | Joutras et al. ................. 482/114 |
| 6,239,784 | B1 | 5/2001 | Holmes |
| 6,397,496 | B1 | 6/2002 | Seymour |
| 6,524,110 | B1 | 2/2003 | Eastwood |
| 6,666,796 | B1 | 12/2003 | MacCready, Jr. |
| 6,746,248 | B2 | 6/2004 | Eastwood |
| 6,853,965 | B2 | 2/2005 | Massie et al. |
| 7,004,494 | B2 | 2/2006 | Wulf et al. |
| 7,153,242 | B2 | 12/2006 | Goffer |
| 7,164,967 | B2 | 1/2007 | Etienne-Cummings et al. |
| 7,190,141 | B1 * | 3/2007 | Ashrafiuon et al. ..... 318/568.12 |
| 7,549,969 | B2 * | 6/2009 | van den Bogert ............... 602/16 |
| 7,571,839 | B2 * | 8/2009 | Chu et al. ...................... 224/637 |
| 7,833,134 | B2 * | 11/2010 | Gordon ........................... 482/52 |
| 7,845,017 | B2 * | 12/2010 | Godshaw et al. .................... 2/24 |
| 2002/0094919 | A1 | 7/2002 | Rennex et al. |
| 2002/0110793 | A1 | 8/2002 | Eastwood |
| 2003/0093021 | A1 | 5/2003 | Goffer |
| 2003/0223844 | A1 | 12/2003 | Schiele et al. |
| 2004/0106881 | A1 | 6/2004 | McBean et al. |
| 2005/0108900 | A1 | 5/2005 | Knowles |
| 2005/0251079 | A1 | 11/2005 | Carvey et al. |
| 2006/0046907 | A1 | 3/2006 | Rastegar et al. |
| 2006/0046908 | A1 | 3/2006 | Rastegar et al. |
| 2006/0046909 | A1 | 3/2006 | Rastegar et al. |
| 2006/0046910 | A1 | 3/2006 | Rastegar et al. |
| 2006/0064047 | A1 | 3/2006 | Shimada et al. |
| 2006/0247904 | A1 | 11/2006 | Dariush |
| 2006/0260620 | A1 | 11/2006 | Kazerooni et al. |
| 2007/0061016 | A1 | 3/2007 | Kuo et al. |
| 2007/0123997 | A1 | 5/2007 | Herr et al. |

FOREIGN PATENT DOCUMENTS

| | | |
|---|---|---|
| EP | 1 400 438 A2 | 3/2004 |
| ES | 295785 | 5/1988 |
| FR | 1549497 A | 12/1968 |
| WO | 2005/092452 A1 | 10/2005 |
| WO | 2006/107716 A2 | 10/2006 |
| WO | 2006/113520 A2 | 10/2006 |

OTHER PUBLICATIONS

Pratt, Jerry E. et al. "The RoboKnee: An Exoskeleton for Enhancing Strength and Endurance During Walking" Proceedings of the 2004 IEEE Int'l Conf. on Robotics & Automation Apr. 2004.

CBC News website "Scientists invent bionic boots to ease load for soldiers" Mar. 11, 2004 (http://www.cbc.ca/health/story/2004/03/11/bionic_boots040311.html, viewed Jun. 4, 2007).

Gordon, K.E., Ferris, D.P., Learning to walk with a robotic ankle exoskeleton. Journal of Biomechanics (2007), doi:10.1016/j.jbiomech.2006.12.006.

Kramer, Andrew E., "Gas-Powered Footwear's Fate Shows Frustrations of Russian Inventors" New York Times Mar. 17, 2007 p. C1.

Kramer, Andrew E., "These Boots Were Made for 22 M.P.H." New York Times Mar. 17, 2007 p. C1.

International Search Report for PCT/ES2008/000243 dated Aug. 7, 2008.

* cited by examiner

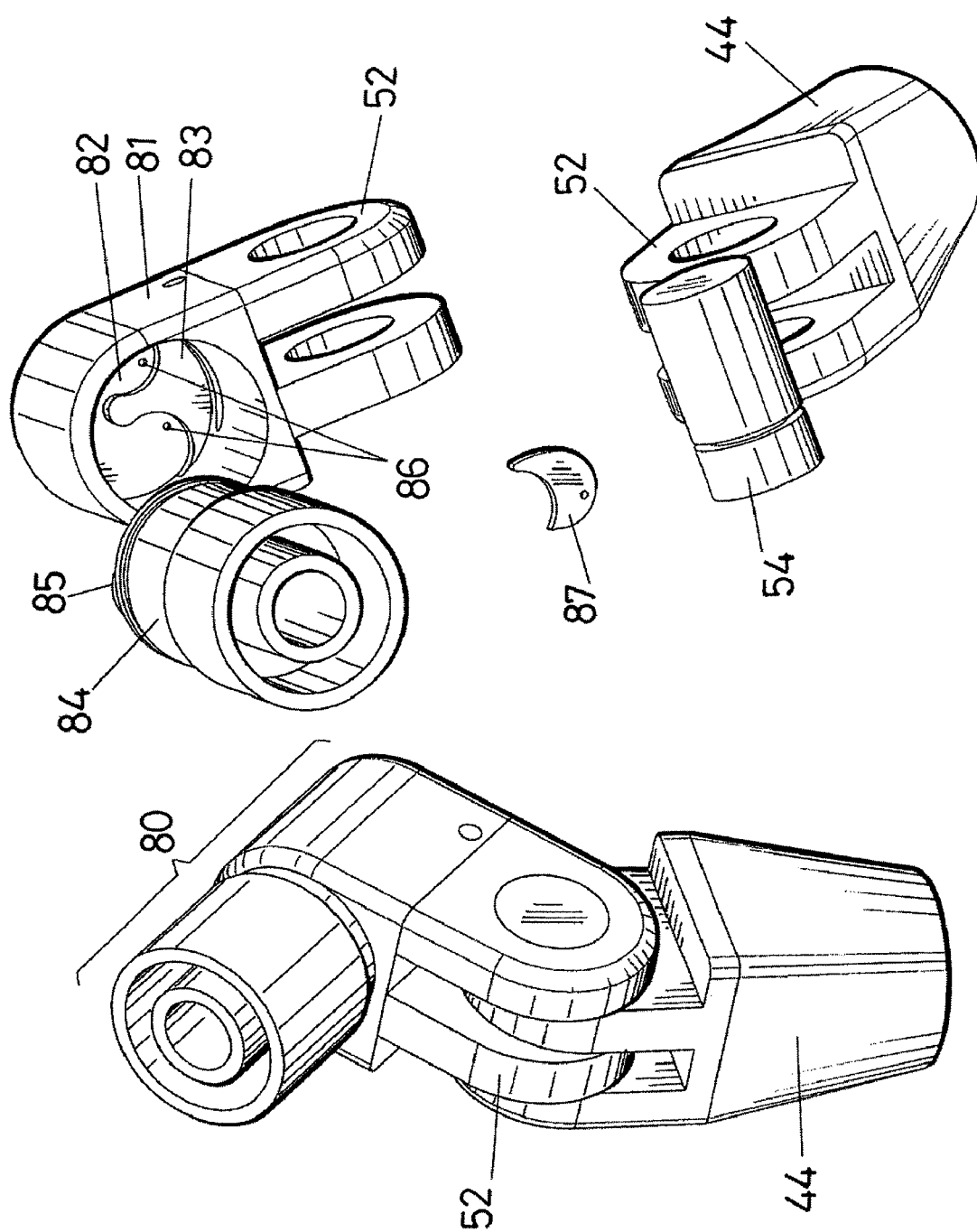

EXOSKELETON

This application is a continuation of International Application No. PCT/ES2008/000243, filed Apr. 14, 2008; and claims the benefit of U.S. Provisional Application 61/035,918, filed Mar. 12, 2008; U.S. Provisional Application 61/035,924, filed Mar. 12, 2008; U.S. Provisional Application 60/907,914, filed Apr. 23, 2007; and U.S. Provisional Application 60/907,913, filed Apr. 23, 2007, their entire contents of which are incorporated herein by reference.

TECHNICAL FIELD

The present invention relates to an exoskeleton or safety device for physical activity, especially snow skiing, making such physical activity safer. The exoskeleton is particularly beneficial in protecting against knee injuries, as this is the joint that suffers the most damage in accidents that occur while practicing sports, such as skiing. Nevertheless, the protection provided by the exoskeleton of the present invention is not limited to the knee, but can provide protection to other parts of the body, including the entire leg. For example, the exoskeleton of the present invention can provide protection up to a skier's hip or in certain embodiments up to the skier's thigh.

As noted, the present invention is especially beneficial for skiing, particularly downhill skiing, although the present invention may also be useful for other sports involving the risk of joint or bone injury. Therefore, everything that is explained below could also be used, with the logical adaptations, for the protection of other athletes and people who practice activities that involve the risk of physical injuries in general and joint injuries in particular.

BACKGROUND

Every year downhill skiing causes many serious knee injuries involving ligament and meniscal tears, despite the efforts that have been made in the industry to improve the bindings, and therefore the skier's attachment to the skis.

These injuries often force persons to quit skiing or practicing many other sports. Alternatively, injured persons elect to undergo major surgery that have various risks, are often very painful, involve long recoveries of about six months, and force changes in lifestyle with work, family, professional, psychological and financial drawbacks resulting from the injury.

Other possible injuries while skiing, which follow knee injuries in frequency of occurrence, are head and face injuries, but the use of a helmet to protect against these injuries is becoming increasingly widespread.

Currently, the annual total number of skiers per year between the United States and Europe is about 20 million.

The total number of accidents involving serious injuries entailing caring for and evacuating the injured person from the slope is about between two and four per every thousand. Out of one thousand days skied by a skier, one will be injured between two and four times (in the United States, this figure is about 3.5 per thousand days).

As previously mentioned, skiing involves a high risk of knee ligament and meniscal injuries (between 30% and 40% of the total), among other injuries. Such injuries are frequently caused by the large forces that knees are subjected to because of the stress transmitted to the knee through the rigid boot from the skis, which act as large levers as illustrated in FIG. 1A.

There are different knee injuries, but the most common ones in skiing are external lateral ligament tears (between 20 and 25% of injuries) and the anterior cruciate ligament tears (between 10 and 15% of injuries).

The injury to the external lateral ligament normally affects beginners and intermediate level skiers, who ski mainly in the wedge position, with the feet facing inwards, and who are injured during a fall, when the skis cross over one another or when the wedge opens up. Injury to the external lateral ligament can occur in more experienced skiers when, for example, a ski strikes against an obstacle or when the ski opens up and the skier tries to counter this movement with his leg.

The injury to the anterior cruciate ligament can occur under different conditions, especially in more experienced skiers, and mainly when:

the rear part of the ski acts as a lever with the boot, exerting a torsion force, twisting and bending the knee;

the skier falls backwards during a jump, he or she instinctively straightens his or her leg and therefore falls on the rear part of the ski, forcing the rear part of the boot against the calf, thus diverting the tibia under the femur and tearing the cruciate ligament; or the skier is upright and is hit from behind on the lower part of the leg, forcing the tibia forwards with the subsequent damage to the cruciate ligament.

Other injuries include damage to the meniscus (between 5 and 10% of all injuries), caused by torsional stress applied to the flexed knee and usually caused when an obstacle is struck at a high speed.

Currently, bindings holding the boot to the ski are relied upon for reducing the risk of injury, but they do not adequately prevent such risk. Bindings are designed so that the boot is released from the ski when a specific and previously established pressure is surpassed. However, depending on the posture of the leg at the time of the demand of the force and of other factors such as the severity of the impact, it is possible that the binding doesn't behave as expected. In such cases, the binding does not come undone and the boot is not released from the ski at the appropriate time or at all, frequently causing the ligaments of the knee to tear before the mechanism can release the boot.

As previously mentioned, these knee injuries usually bring about an expensive surgical intervention with a long and uncomfortable recovery, results that are not always satisfactory and with significant repercussions in terms of work, family, etc.

Conventional devices do not provide the protection provided by the exoskeleton of the present invention.

For example, U.S. Pat. No. 4,136,404 B1 describes an athletic leg brace apparatus, such apparatus being connected to the sides of a ski boot and including a division of the leg that is hinged at the height of the knee, such that the upper part is attached to the thigh and the lower part to the boot. This apparatus allows flexion and extension movement of the leg, restricting the lateral flexion of the two parts of the leg and allowing the transmission of lateral forces of the skier's legs to the lateral parts of the boot. In other words, the problem to be resolved by this device is the reduction of the lateral flexion of a skier's legs while skiing, and eventually protecting the bones of the leg, not the joints, in the event of flexion but not in the event of torsion, which is the stress causing the most common and significant knee injuries, especially when the knee is extended. Another limitation of the apparatus described in the foregoing US patent is that, since the leg is firmly attached to the boot by this apparatus, when the knee is flexed the freedom of movements is quite compromised, affecting the skiing experience, unlike the device according to the present invention.

U.S. Pat. No. 3,947,051 B1 describes a binding for a ski boot with a transmitter located between the skier's leg and boot to initiate the "release" operation of the binding during falls, particularly forward falls. The transmitter detects an excessive force between the leg and the boot, and transmits an instruction to release the binding, preventing leg injuries in the skier. However, as will be understood, the present invention is completely different from the foregoing patent. For example, according to embodiments of the present invention:

there is not requirement for the replacement of the boot-ski binding mechanism, but rather is complementary to it;

the apparatus is not limited to the boot-ski attachment, but rather may include boot-leg-hip or boot-leg-thigh connecting elements referred to herein as an exoskeleton;

the torque generated in the foot due to the lever effect of the ski in dangerous positions of the knee joint is transmitted to the entire exoskeleton structure and through it to the strong areas of the body, such as to the skier's hip or waist; although it may be transmitted to a part of the skier's leg, such as the thigh;

the device, being attached to strong areas of the body, can withstand the torque generated in the foot due to the lever of the ski in limit to extreme positions that may injure the knee, such that resultant forces are not transmitted to the much weaker knee joint, and which until now no system or mechanism has been able to effectively protect as proven by the previously mentioned injury statistics;

the corporal structure in the areas of the body that are most involved in skiing are significantly reinforced, which allows adjusting the setting of the bindings more tightly with the assurance that no injury will occur; because in most cases the skier would be supported by the reinforced structure of the exoskeleton, and in extreme cases, the binding would come undone without affecting the structure of the knee or any other leg joint or bone.

None of the previous functionalities are present in U.S. Pat. No. 3,947,051-B1, whereas the present invention allows one to achieve these functionalities.

United States patent application publication number US 2006260620 A1 describes a lower extremity exoskeleton that is linked to a person and configured such that the two leg supports contact the ground to provide support when the user is stopped. The exoskeleton is formed by a link in the thigh, another one in the calf and two joints at the height of the knee, these joints allowing the extension and flexion of the thigh link and of the calf link. The exoskeleton is attached to the hip through joints allowing extension and flexion. The energy for moving the exoskeleton is provided by the user. This device can be used by persons who require aid in walking or who need to be stopped while bearing and carrying loads. That is, the purpose of the device described in United States patent application publication number US-2006260620-A1 is to increase the user's ability to bear large weights when he or she is walking or is stopped.

International patent application number PCT/US2006/014227, describes a variant of the previously described device further incorporating a motor so as to achieve a greater increase in the strength of the person using the exoskeleton.

United States patent application number US 2006260620 A1, which includes an anchoring to the hip, is structured to achieve results that are different from those of the present invention. As previously noted, this application is directed to a system for increasing the ability to bear large loads, to rest while standing or to substitute the lack of strength in weak legs. As such, this system is not useful for practicing a sport that is as dynamic and that requires as much flexibility as, for example, skiing. Rather, it merely has the purpose of increasing the load capacity, whereas, as explained in this specification, the present invention is structured to increase resistance, not strength, against such things as unwanted rotations of a ski.

The system described in United States patent application publication number US 2006260620 A1 is designed to work vertically with movements similar to those carried out while walking, counteracting forces of gravity, but not to resist rotational movements in a horizontal plane, like the invention described herein, which is particularly applicable for snow skiing.

The hip joint described in United States patent application number US 2006260620 A1 does not have a mechanism allowing rotation about all the natural axes and at the same time limiting the potentially injurious angular movement of the knee. On the other hand, the present invention provides a mechanism especially designed to allow all the freedom of movement necessary for such activities as skiing, while preventing unnatural movements that may cause injuries. The present invention is particularly useful for protecting against extreme rotations of the foot, being designed to support rotational forces or torques due to the large lever that is attached to the skier's leg, i.e., the ski, which situation does not occur in the application of the device described in United States patent application publication number US 2006260620 A1.

The knee joint and ankle joint of the device described in United States patent application number US 2006260620 A1 do not have any mechanism allowing the natural movements necessary for activity such as skiing, and which at the same time protects the joint against movements or positions of the knee in particular, and the leg in general, that can cause injuries. On the other hand, the present invention does provide these mechanisms in the joints, on one hand to provide all the necessary range of movements and on the other hand to limit or prevent those movements or positions that may be injurious to the leg in general and the knee in particular, especially focusing on the protection against severe rotations of the foot, or of the body around the foot, which may occur involuntarily during physical activities such as skiing.

SUMMARY OF CERTAIN ASPECTS OF THE INVENTION

Due to its unique structure, the exoskeleton or safety device of the present invention solves problems and inconveniences or disadvantages not solved in the state of the art, mainly due to the fact that these problems had not been set forth and never raised therein until now, due to the fact that the known devices do not prevent the possibility of knee injuries. Rather, the known devices merely reduce the possibility of knee injuries in very particular and very determined operating conditions, that are specific to each device, unlike the present invention which prevents leg and hip injuries and, especially, knee injuries. The device of the present invention allows the diversion of the potential forces that might cause damage (FIG. 1B), generally in the legs and specifically in the knees, to strong parts of the body as the hip and to the more resistant parts of the legs. When the movement arrives to a dangerous anatomical position, is the exoskeleton which resists the generated forces and diverts them to the stronger parts of the leg and hip. These forces are specially, although not exclusively, the ones produced by the large lever represented by the ski that in another situation would cause serious injuries in the knee.

An object of the present invention, therefore, is to provide an exoskeleton (safety device) that prevents injuries due to torsion of the knees, legs and hip, while a person engages in physical activity, such as skiing. The exoskeleton of the present invention achieves this object by diverting the stress, and particularly the excessive torsional forces that could result in injuries (FIG. 1A) through a support structure or exoskeleton attached to the strong areas of the waist and/or legs, ensuring that the knee in particular does not suffer from such stress (FIG. 1B).

In one exemplary embodiment, the exoskeleton of the present invention transmits the torque caused by the large lever, the ski, from a support member (second support member) of the exoskeleton configured to couple the exoskeleton to the skier's body below the knee, for example a rigid boot, to strong areas of the body through another support member (first support member) of the exoskeleton that is coupled to the skier's body above the knee. Through the structure of the exoskeleton, the weaker ligaments of the knee are protected from an overload caused by the lever (i.e., the ski).

According to one object of the present invention, the exoskeleton includes:
- a first support member that couples the exoskeleton to the user's body above the knee, such as the hip or the thigh;
- a second support member that couples the exoskeleton to the user's body below the knee, such as the boot, the binding of the boot to the ski or the ski itself;
- a first linkage or linkage assembly with two ends, an upper end coupled to the first support member and a lower end coupled to the second support member, the first linkage assembly extending along the leg of the person or skier wearing the exoskeleton; and
- at least one first rotation limiting joint or angle of rotation limiting mechanism (ALM) that limits the relative rotation or torsion between the first support member and the second support member about the axis linking them together, thus limiting the relative rotation or torsion between the coupling point to the body of the first support member and the coupling point to the body of the second support member.

Therefore, in an embodiment of the present invention, the exoskeleton is coupled to one or to both legs of a skier or person using the exoskeleton, a first coupling to the skier's body above the knee and a second coupling to the skier's body below the knee. A mechanism (ALM) is arranged between the first coupling and the second coupling, limiting the relative rotation or torsion between the coupling point to the body of the first support member and the coupling point to the body of the second support member.

This ALM or Angle Limitation Mechanism can be regulated so that the person using the exoskeleton can determine the exact degrees that the first support member can rotate in respect of the second support member.

The first support member is preferably located at the height of the waist where relative torsion between both feet, that are connected by the exoskeleton through the hip, is further limited, although it is possible to use a first support member in each leg or only in one of the legs, such that such first member can also be located at the skier's thigh or thighs.

The device can also have joints or mechanisms between two elements of the exoskeleton such that they can transmit torque between those two elements connected by the joints, allowing the torque transmission independently of the angular alignment between the respective torque axis of both elements. Examples of these joints or mechanisms include certain elastic joints or universal joint-type transmissions, cables of the type employed in odometers, among others.

Therefore, several variants of the exoskeleton of the present invention allow the transmission of the torque from the coupling to the skier's body below the knee, from and through the second support member, to the coupling to the skier's body above the knee, through the first support member, wherein the upper coupling may be located above the knee at, for example, the skier's hip or waist or the skier's thigh or thighs.

In view of the foregoing, the device according to one embodiment can be described as a structure that, by way of an exoskeleton, fixes the second support member (e.g., the skier's boot, the binding of the boot to the ski or the ski, by articulated elements allowing freedom for natural movements of the legs) to a structure that is attached to the legs and can encircle, by way of the corresponding first support member, the skier's hip or the skier's thigh.

In this manner, while the rotation or torsion of the legs is permitted to move within the "safe" angular range that the skier's physical joints naturally allow, the structure neither hinders nor limits natural and safe movement of the skier. However, as a result of specially designed mechanisms, when the angle of rotation approaches what may be injurious for the knee, the structure of the exoskeleton works as an abutment and reaches a rigid point, such that the rotation of the second support member, preferably the boot, stops and is withstood by the entire support structure, namely: the exoskeleton itself and the strong areas of the legs above the knee (e.g., the waist or the thigh). The resistance of a skier's legs to dangerous torsional forces is thus significantly increased, as the skier now has a chain of strong links protecting the weaker knee joint. This allows the skier to ski with more energy and with more confidence, being sure that his or her knee will not be subjected to the torsional stress due to the ski acting as a lever, since such stress will now avoid or bypass the knee through the exoskeleton. This will in turn allow skiing with tighter settings of the bindings, with greater safety and with no risk of injuries. As a last resort, if the extreme case in which the binding must be released is reached, it will always do so upon the demand of this structure and not of the knee joint. This same structure can also prevent other types of injuries, such as thigh or tibia bone fractures, and in most of the preferred embodiments which include a first support member surrounding the hip or waist, even hip injuries, among others.

The aforementioned possibility of an optimal setting of the bindings is extremely important. In the current state of the art, the existing bindings force the skier to choose between a "loose" setting or a "tight" setting, it being very difficult to achieve the optimal setting. A setting that is too loose will make the skier lose a ski in an inconvenient situation, which could cause an injury. A setting that is too tight entails the risk of the skier's leg suffering severe injuries because the binding does not release the ski before reaching the injury point. What is worse is that even with "loose" settings it is by no means ensured that the bindings will be released in certain situations.

The linkage assembly can be split into two parts or two independent linkage assemblies, an upper linkage assembly and a lower linkage assembly. In this case, the linkage of the first support member with the second support member is carried out through an artificial joint about the knee, linking the first support member with the artificial joint about the knee through an upper linkage assembly and the artificial joint about the knee with the second support member through a lower linkage assembly. This artificial joint is located at the same height as the natural joint of the skier's body or person using the exoskeleton. These upper and lower independent linkage assemblies can likewise be attached by belts or straps to strong areas of the legs, encircling them, and the part at the waist can encircle the waist or the hip. The mentioned linkage assembly, split into two independent linkage assemblies or not, can be replaced or combined with anatomical parts adapted to the shapes of the skier's leg, both standardized and custom-made, and made of fiber, plastic or any industrially available materials today, or those materials which in the future may be useful for the intended function. Accordingly, the device forms an exoskeleton from a point located above the knee, preferably the hip or the thigh, to the feet.

The linkage assemblies can also connect the first support member and the second support member directly without the need for an artificial joint in the knee, preferably by an extendible linkage assembly.

Accordingly, the present invention provides artificial joints allowing natural movement of the human body as well as structure limiting the amount of relative rotation or torsion between the anchoring point of the first support member and the anchoring point of the second support member, preventing the rotation of the knee from continuing when the skier surpasses the potential injury limit. The structure thereby transmits the torque as desired, transmitting it out of the knee and making the skier's legs much more resistant to the torque generated by the action of the ski and to other forces generated while practicing this sport or other physical activities that can cause different types of injuries. With such a device, the skier's second support member, or preferably the boot of the skier or user of the exoskeleton, is connected to the first support member or part surrounding the hip or waist by the linkage assembly.

Some versions of the exoskeleton incorporating the first support member at the hip or waist can also incorporate at the height thereof a device limiting the flexion, extension, abduction and adduction of the coxofemoral joint of one or of the two legs of the skier or person using the device.

All the natural movements of the body can be carried out with absolute freedom as a result of the joints, mechanisms or artificial joints, and when the torsion or other potentially injurious movements approach the natural movement limit point, e.g., when they approach the point at which the ligament, bone or meniscus would tear without protection, the system withstands the impact, thus protecting the leg, overall, and the joint, in particular, as a result of the angle or rotation limiting mechanisms. As has been described when a lower extremity is subjected to a rotation that is close to the injury point, the angle limiting mechanisms limit further rotation, making rigid the structure and transmitting the torque experienced by the extremity to the strong areas thereof and in most of the cases to the hip. Therefore, dangerous torsions occurring both in the longitudinal axis and in the sagittal axis of the extremity are diverted to the rigid structure of exoskeleton, without at all being supported by the natural knee joint and, therefore, preventing torsion thereof as illustrated, for example, in FIG. 1B.

BRIEF DESCRIPTION OF THE DRAWINGS

For the purpose of aiding in understanding the invention, reference is made below to the following exemplary figures of certain preferred embodiments attached to the description in a non-limiting manner:

FIG. 1A shows a skier without an exoskeleton of the present invention and includes a schematic depiction of certain stresses that the skier is subjected to;

FIG. 13 shows an angle limitation mechanism (ALM) with a knee joint and part of the lower linkage assembly;

FIG. 14 shows an exploded view of the elements in FIG. 13;

Figure 1A:
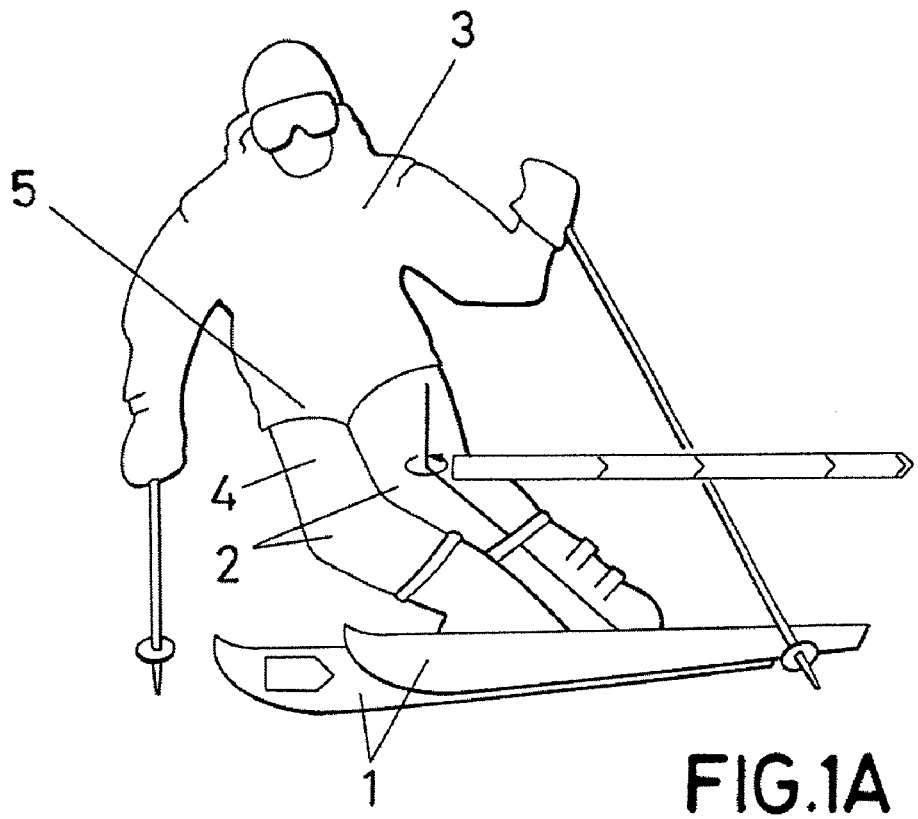
Figure 1B:
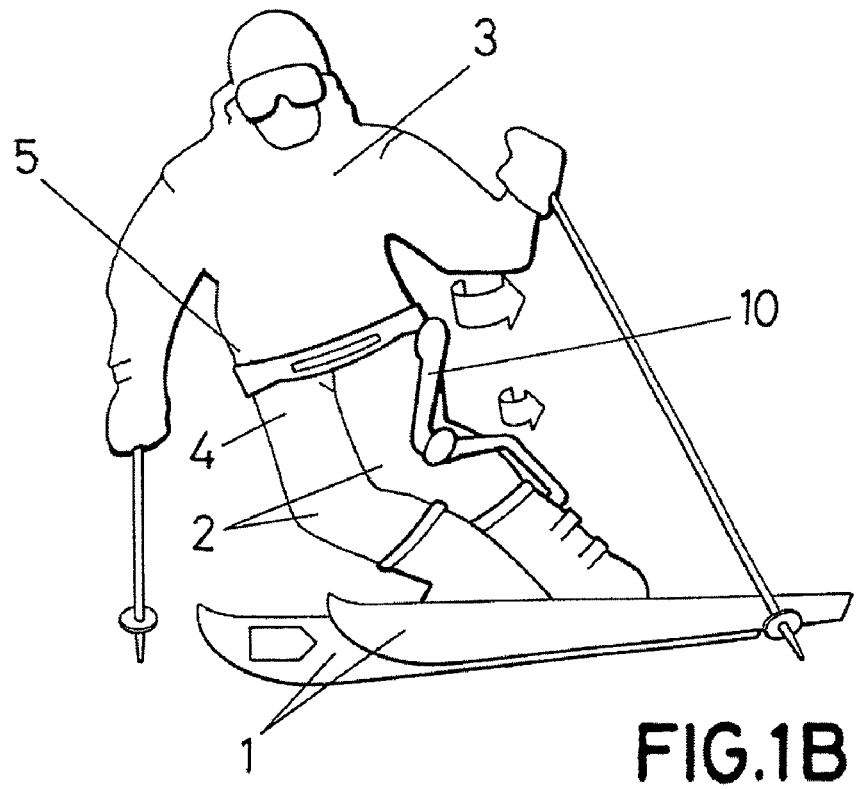
FIG. 1B shows a skier and a schematic depiction of stresses in an exemplary exoskeleton in accordance with the present invention.

DESCRIPTION OF EXEMPLARY
NON-LIMITING EMBODIMENTS OF THE
INVENTION

A description of different exemplary preferred embodiments of the invention for use in snow skiing will be described next. With reference to FIGS. 2, 2B, 2C, 19, 20, 21, 22, 23, the exoskeleton or safety device for snow skiing (10, 11, 12, 13, 14) to be worn by a person (3) over at least one leg includes a first support member (21), preferably rigid, a second support member (31), a linkage assembly (40) between the first support member and the second support member and at least one rotation limiting joint or angle or rotation limiting mechanism (ALM) (70, 80, 90, 110). The exoskeleton can further include artificial joints allowing both the transmission of the torque from the second support member to the first support member, as well as allowing the skier's natural movements.

The linkage assembly (40) located between the upper and lower support members can be split into two subassemblies (41, 44), between the support members, such that the first linkage subassembly is an upper linkage assembly (41) that connects a point above the knee (2) (e.g., the first support member (21) attached to the hip (5) or the first support member (29) to the thigh (4)) to the artificial joint at the height of the knee (2), and the second linkage subassembly is a lower linkage assembly (44) that connects the artificial joint at the height of the knee (2) to the second support member.

The linkage assembly (40) can be located on either leg alone or on both legs at the same time.

Figure 19:
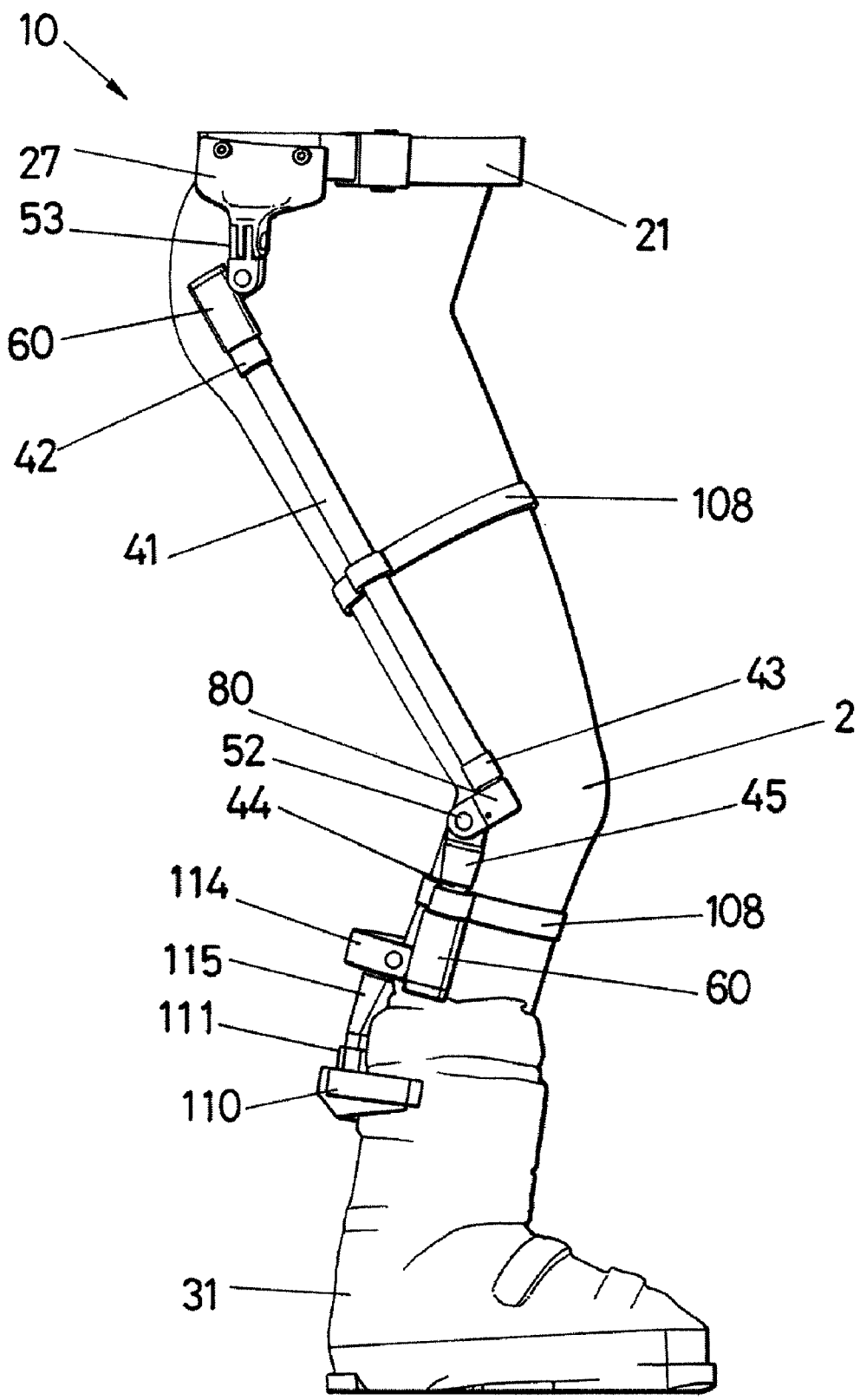
FIG. 19 shows a skier's lower extremities with a first exemplary embodiment of the invention.

In one preferred embodiment (10), shown in FIGS. 2 to 19, the exoskeleton is attached to the body by a first rigid support member (21) coupled to the body above the knee (2). Specifically, a first ergonomic coupling part (21), as shown in FIG. 19, which can be located approximately at the height of the skier's waist or hip (5).

If such a first support member (21) is provided, it can take the form of a rigid belt (21) having two parts (22, 23) specifically linked together to form a rigid whole, thus allowing its opening for coupling to the skier's body along its entire contour, since it surrounds the waist with the belt surrounding part (22) and a belt front part (23). The belt can be clamped by the user at the front with the help of belt connections (24, 25) and a belt closure (26). One of the belt connections (24) is placed on a free end of the belt surrounding part (22) and the other belt connection (25) is placed on the free end of the belt front part (23). The belt connections (24, 25) are partly coupled together, one on top of the other forming one element and the belt closure (26) fixes both belt connections (24, 25) together.

The first support member, in this embodiment the belt (21), is connected to the rest of the exoskeleton through a T element (27) that is secured to the belt surrounding part (22) by screws (28). This T element can also be included as part of the belt surrounding part (22).

The remaining components forming the structure of the exoskeleton can be arranged on both sides of this first support member or belt (21). The lower end of the T element (27) is coupled to the linkage assembly (40), specifically to the upper end of the linkage assembly (41), and more specifically in this embodiment to the upper end (42) of the upper linkage assembly (41) through a joint, specifically a double hinge (53) with pins (54).

This double hinge (53) is preferably made up in such a way that limits, in an adjustable way, the rotation range in each of the two directions of each of its two axis.

The upper linkage assemblies (41) can have a length approximating the length of the femur of an average man and can preferably allow modification of its length to provide an optimum fit using for this purpose a length regulating mechanism or LRM (60) coupled to the joint, in this case a double hinge (53), preferably of limited range The LRM (60), as shown in FIGS. 8 to 12, is used for regulating the length of the upper linkage assembly (41) and includes an LRM inner member (61) or shaft, with hexagonal section, coupled to the upper end of the upper linkage assembly (42) and an LRM outer member (62) or hub, preferably with hexagonal section too, coupled to the joint or double hinge (53) attached to the T element (27). The LRM inner member (61) has holes or the like (63) in outside facing surfaces and the outer member (62) has at least one sphere (64), preferably two, on its lower end. This outer member (62) also has a pressing device (65) inside for pushing the sphere (s) (64), which is maintained in its place by an LRM outer member cover (66). When the sphere (64) is introduced in a hole (63) of the inner member (61) and the pressing device (65) is not pushed, the coupling between the belt (21), through the T element (27) and the double hinge joint (53), and the upper linkage assembly (41) is fixed. In order to modify the length of the linkage assembly (41) and therefore the length of the exoskeleton, the user must press the pressing device (65) to unblock the sphere (64) from the hole (63) and allow the inner member (61) to move along the outer member (62). The movement can be stopped when the sphere (64) is positioned into the desired hole (63) of the inner member (61) when the length desired by the user has been reached. This LRM can also be used to uncouple the upper linkage assembly (41) from the set formed by the belt (21), the T element (27) and the double hinge joint (53).

As shown in FIGS. 2, 2B, 2C, 19, 20 and 21, the upper linkage assembly (41) runs between the hip (5) and the knee (2). The coupling between both members, hip part or T element (27) and upper linkage assembly, is carried out as previously stated, by a joint, preferably a double hinge joint (53) as described, and which can also be a hinge (52), a universal joint or Cardan joint (51) or any other element having similar dynamic features and allowing the angular movements of the leg at the coxofemoral joint at least in the two transverse and sagittal axes, or in other words, allowing flexion, extension, adduction and abduction, while at the same time limiting, preferably in a manner that can be adjusted by the user, the angular movements, i.e. the flexion, extension, adduction and abduction, in said transverse and sagittal axes at values that may by injurious. As already mentioned, the artificial joint placed at the height of the hip is in this preferred embodiment, a double hinge (53) with limited rotation.

Figure 2:
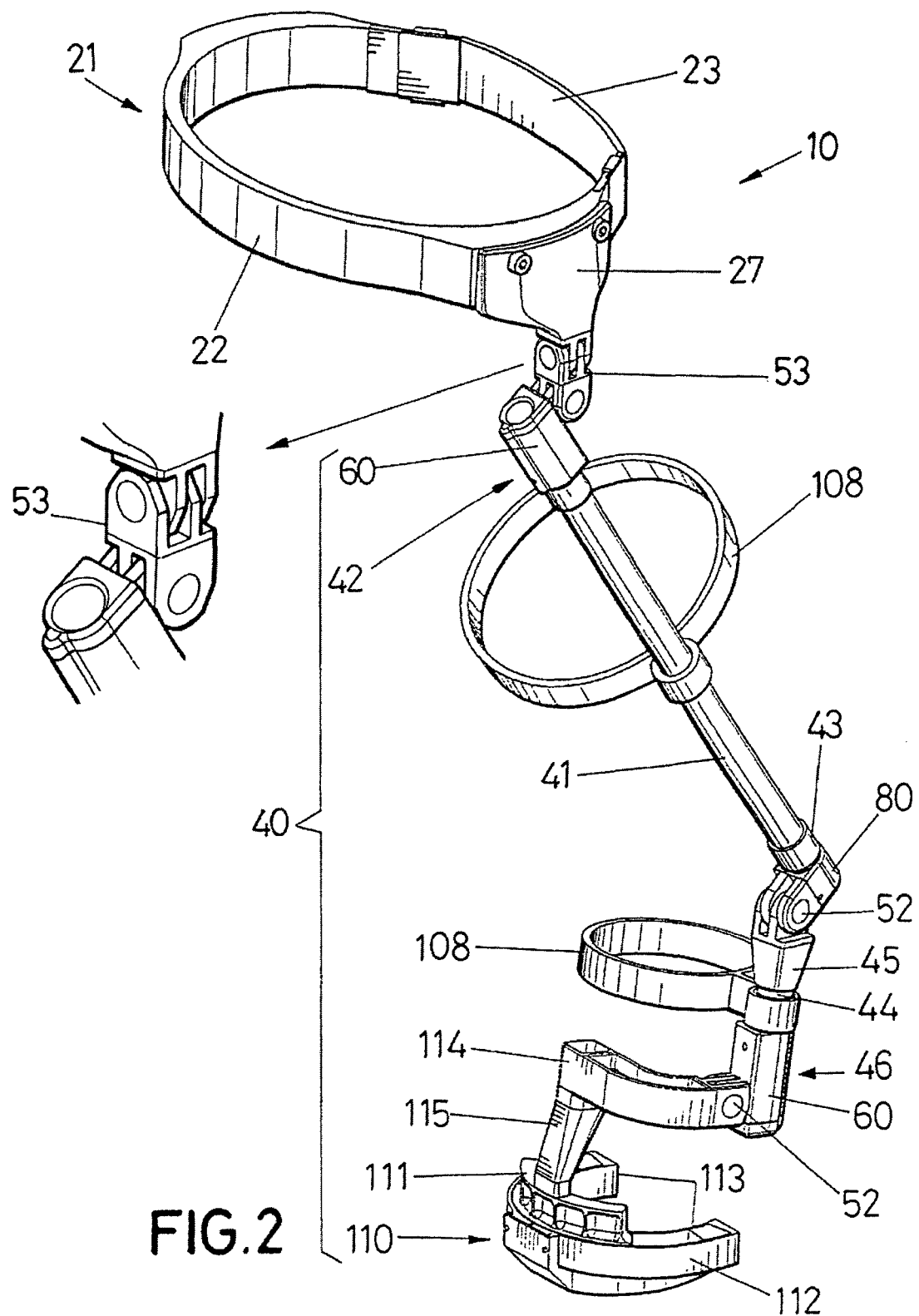
FIG. 2 shows a first preferred embodiment for only one leg, of the two preferred, of an exoskeleton according to the invention.
Figure 2B:
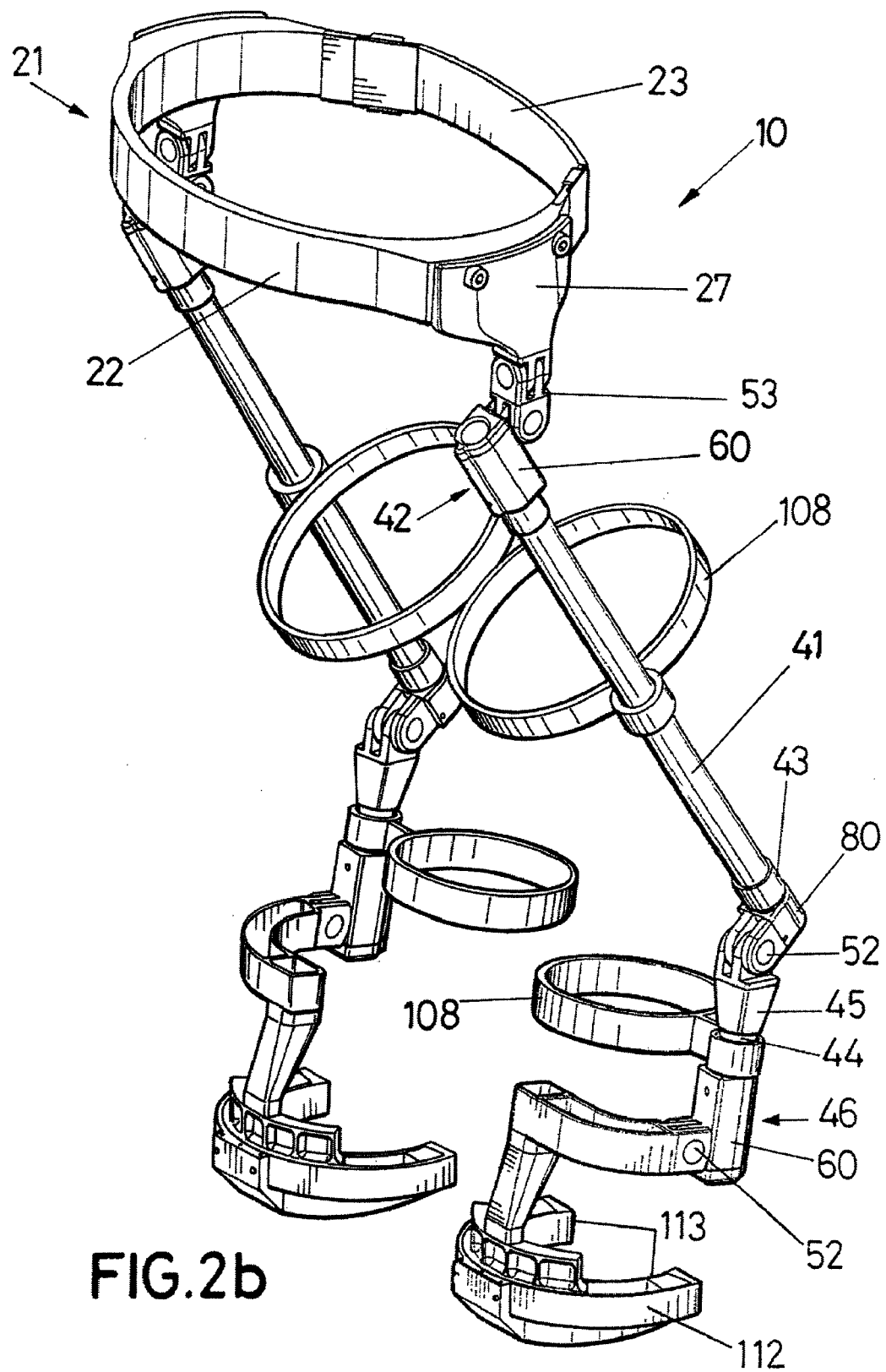
FIG. 2B shows a first preferred embodiment of an exoskeleton with two legs according to the invention.
Figure 2C:
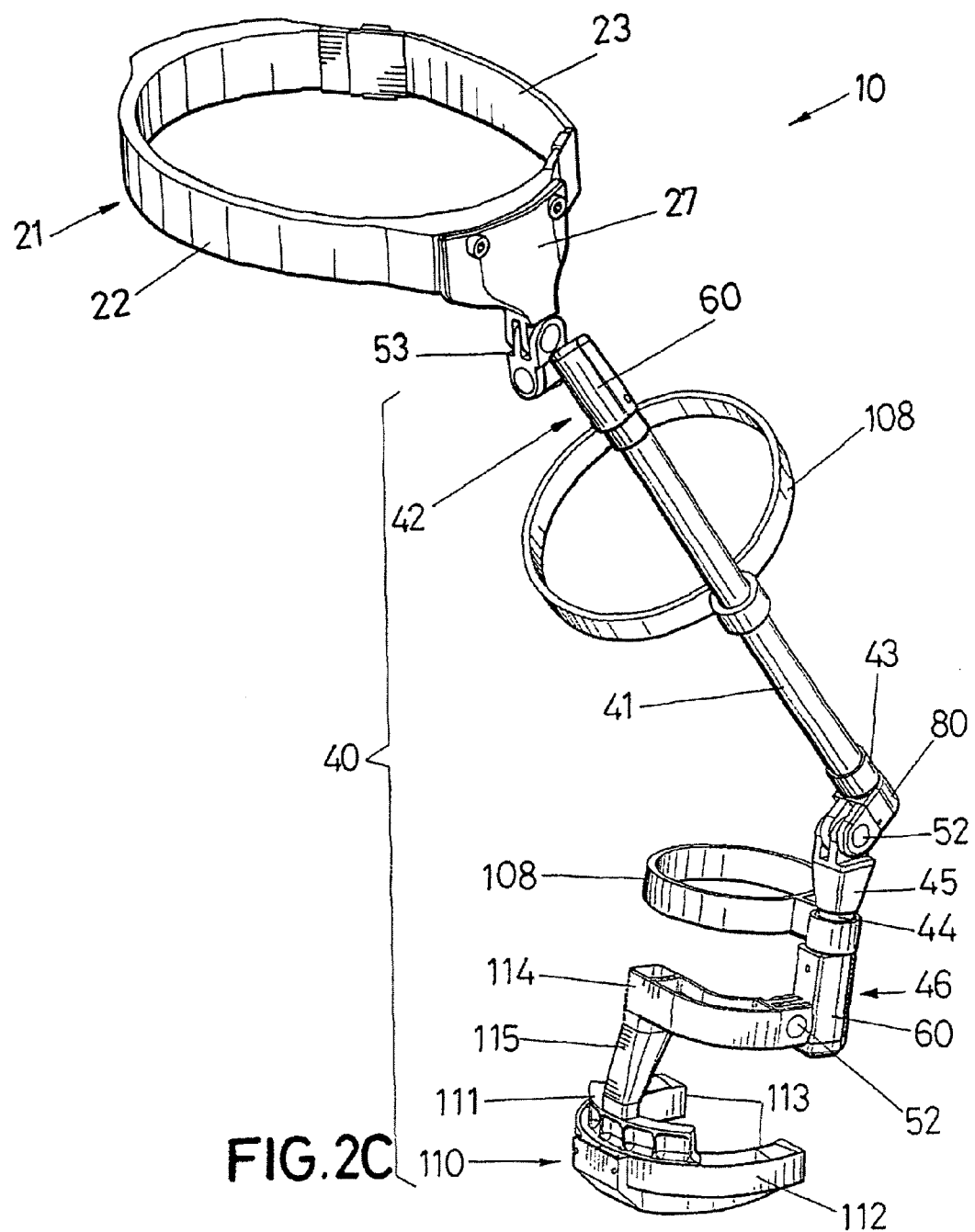
FIG. 2C shows a first embodiment of an exoskeleton as the one shown in FIG. 2, where the double hinge placed at the height of the hip has its two axis turned 90 degrees.
Figure 3:
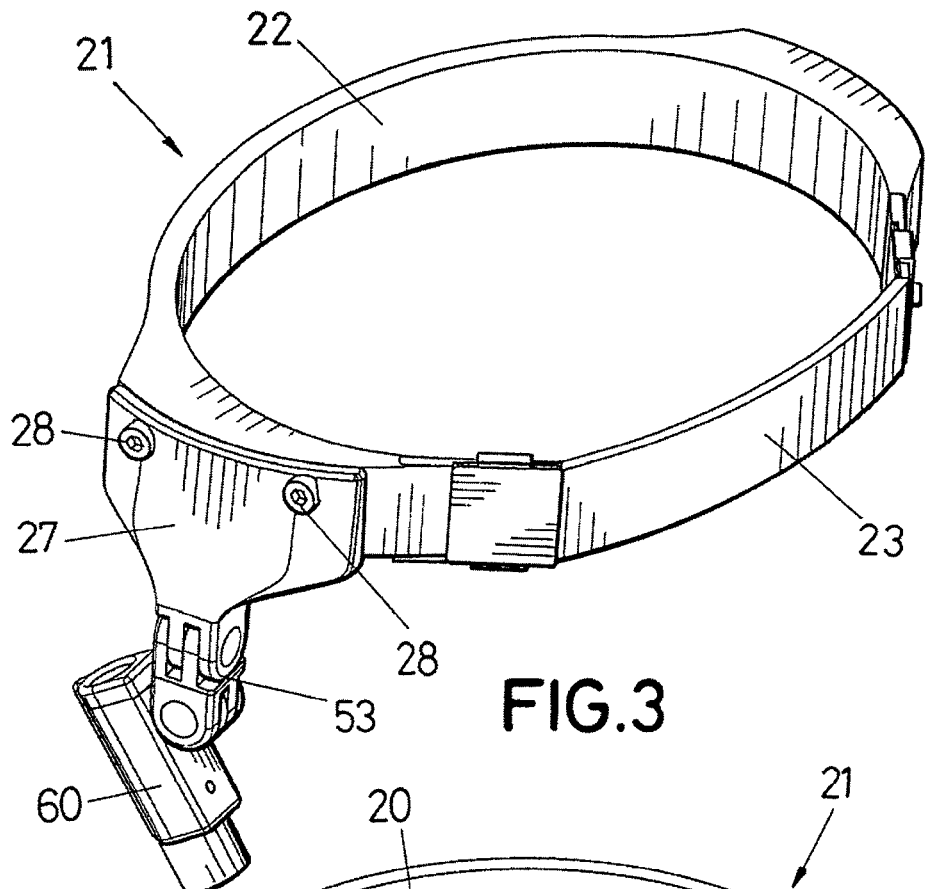
FIG. 3 shows a first support member for the hip/waist and elements for joining to the linkage assembly.
Figure 4:
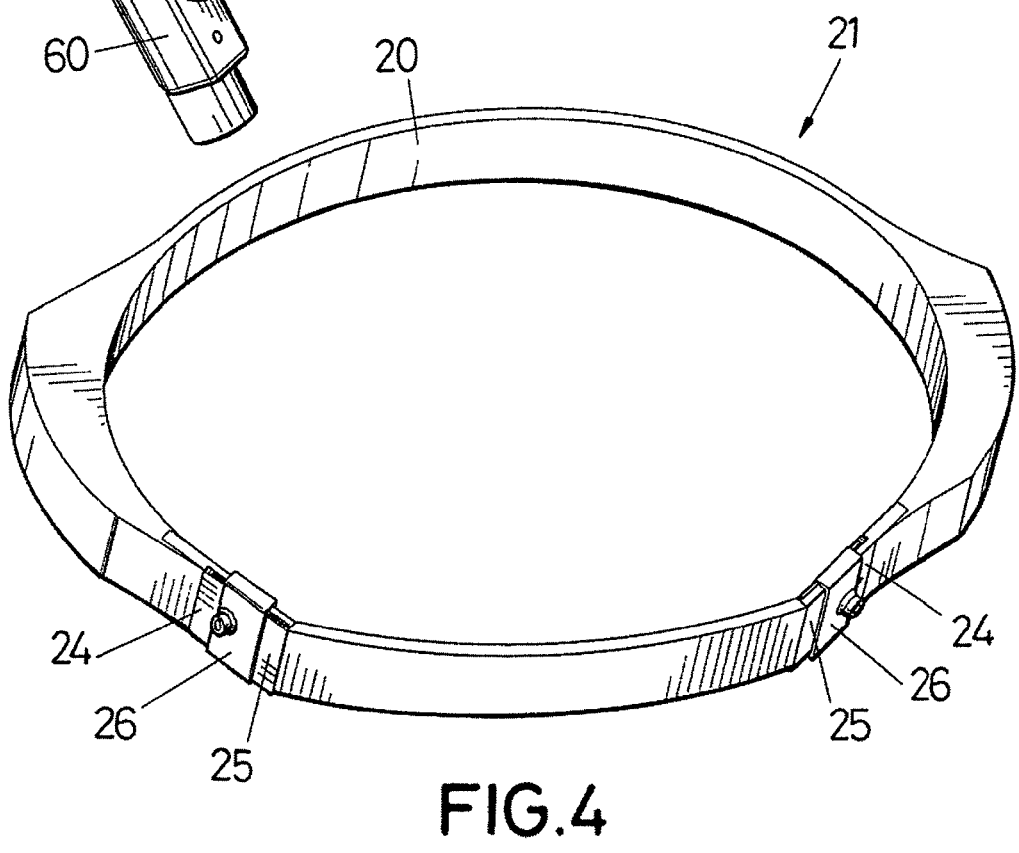
FIG. 4 shows certain details of a rigid belt for the first support member of FIG. 3.
Figure 5:
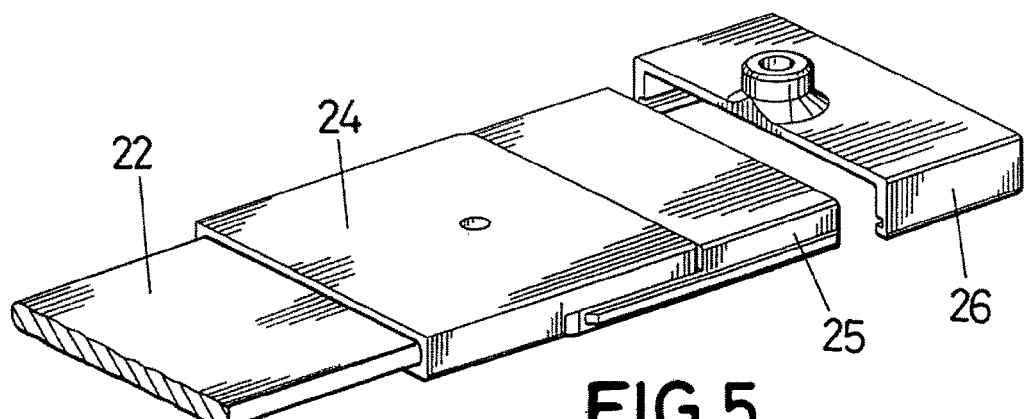
FIG. 5 shows a detail of the connection elements of the rigid belt in FIG. 4 in a stage prior to the connection.
Figure 6:
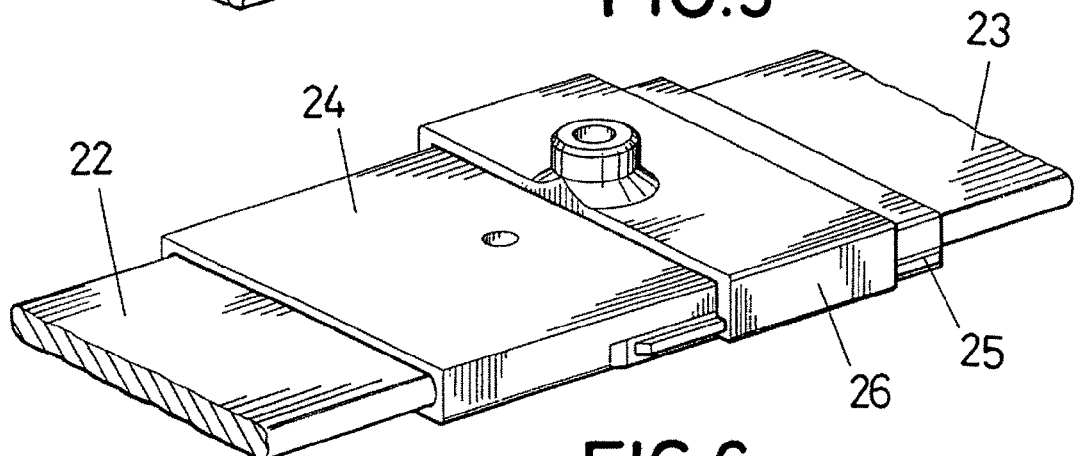
FIG. 6 shows a detail of the connection elements of the rigid belt in FIG. 4 in a further stage prior to the connection.
Figure 7:
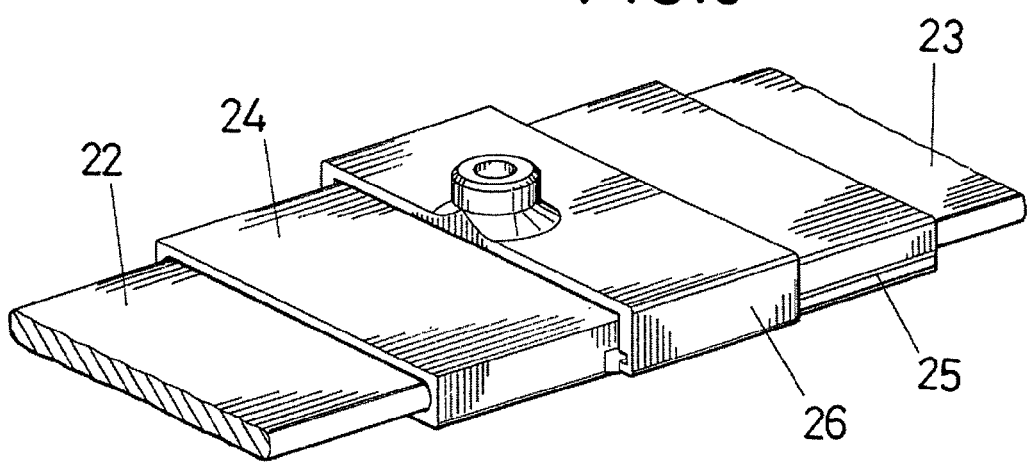
FIG. 7 shows a detail of the connection elements of the rigid belt in FIG. 4 once connected.
Figure 8:
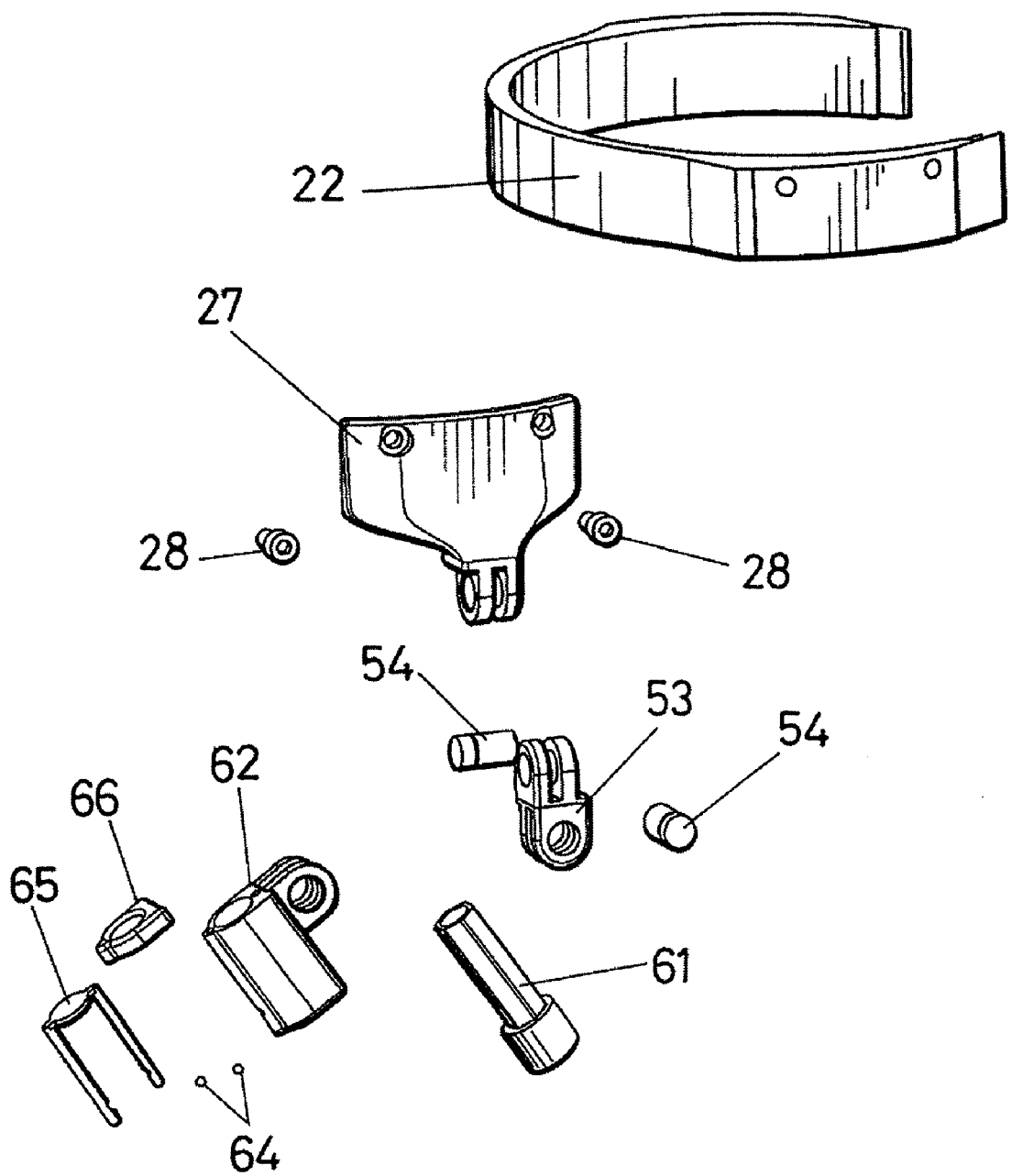
FIG. 8 shows an exploded view of the elements of FIG. 3.
Figures 9, 10:
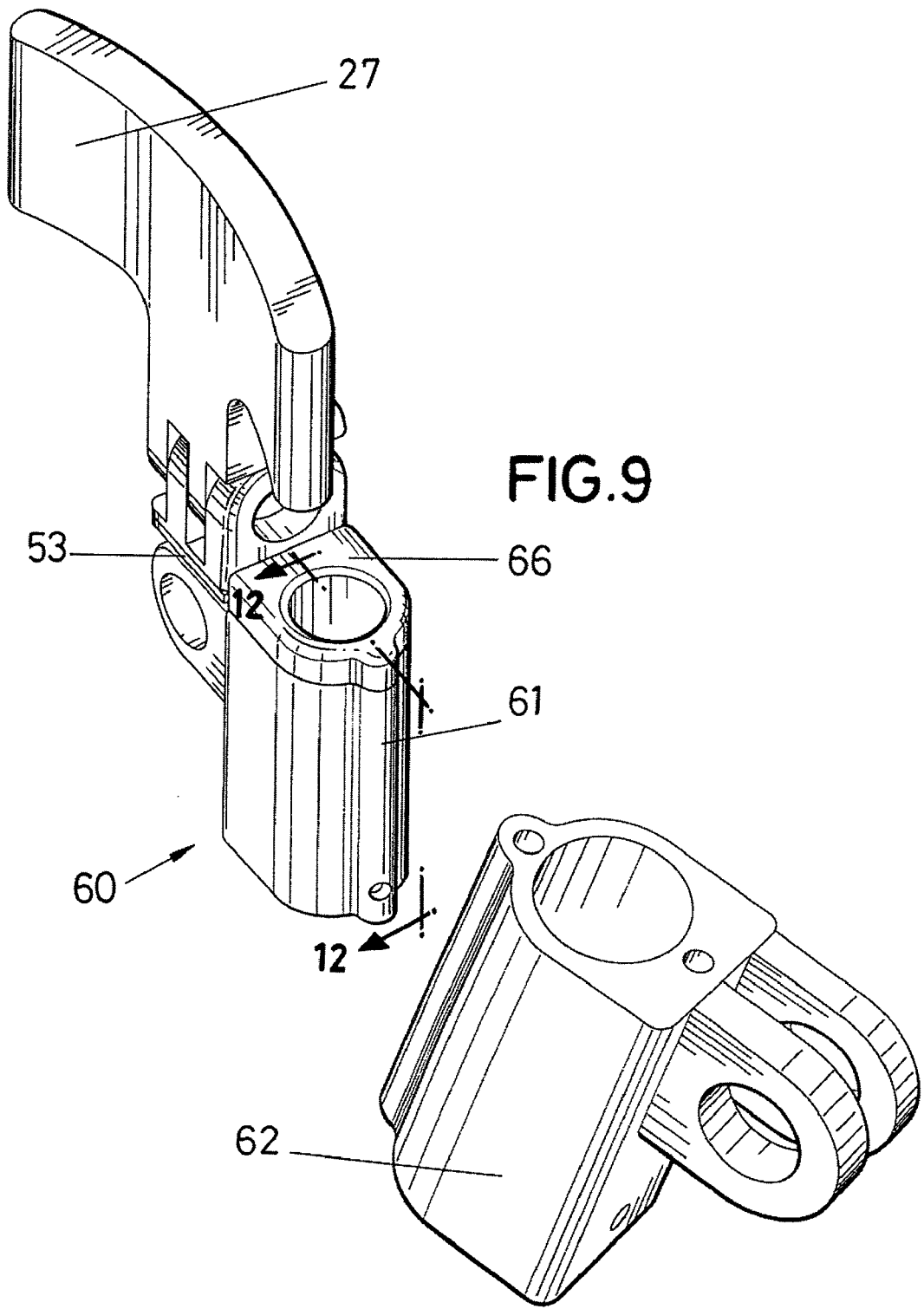
FIG. 9 shows the T element of the rigid belt in FIG. 3 with a double hinge joint and a length regulating mechanism (LRM)
FIG. 10 shows the outer member of the LRM.
Figure 11:
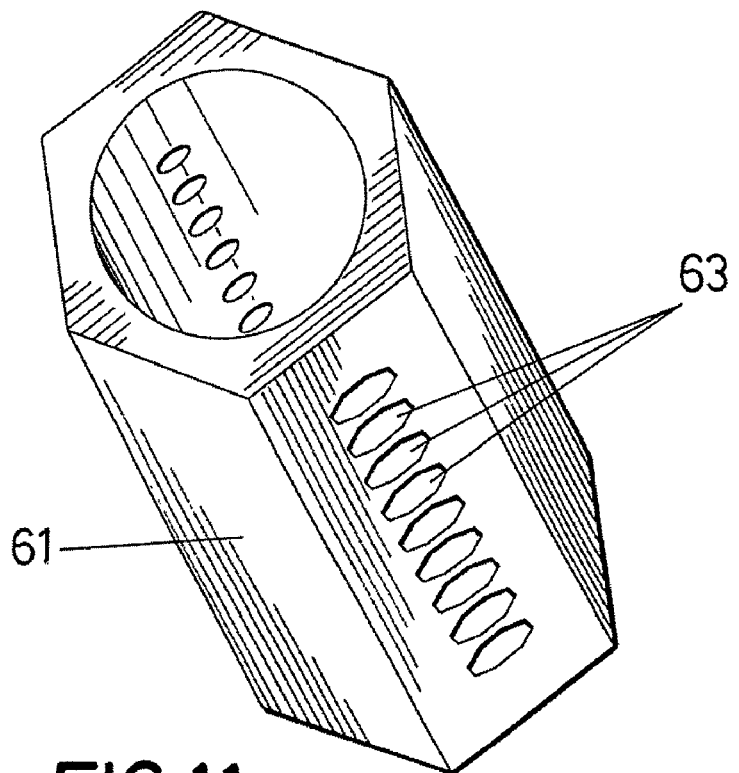
FIG. 11 shows the inner member of the LRM.
Figure 12:
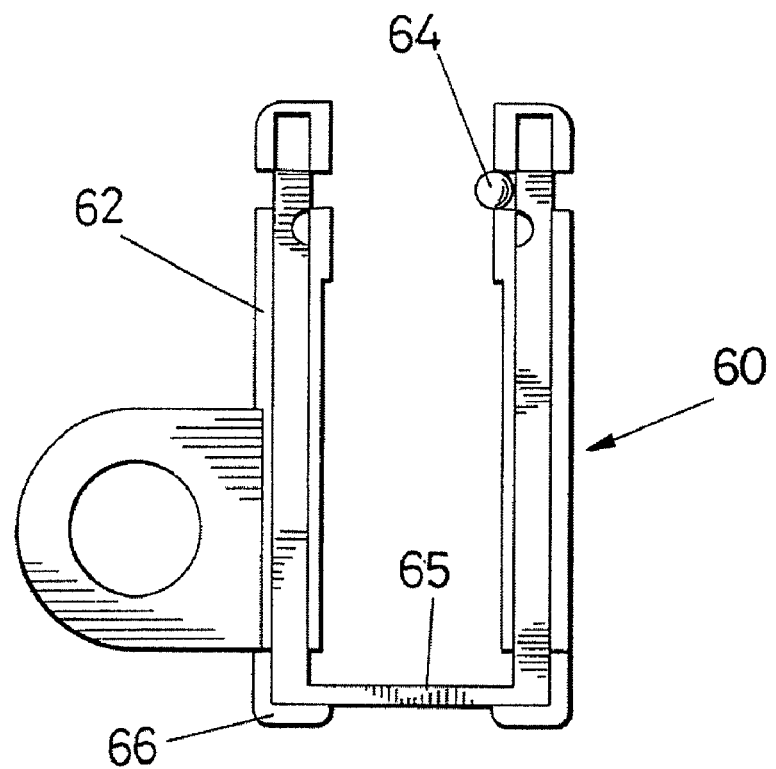
FIG. 12 shows a section view of the LRM.
Figure 15:
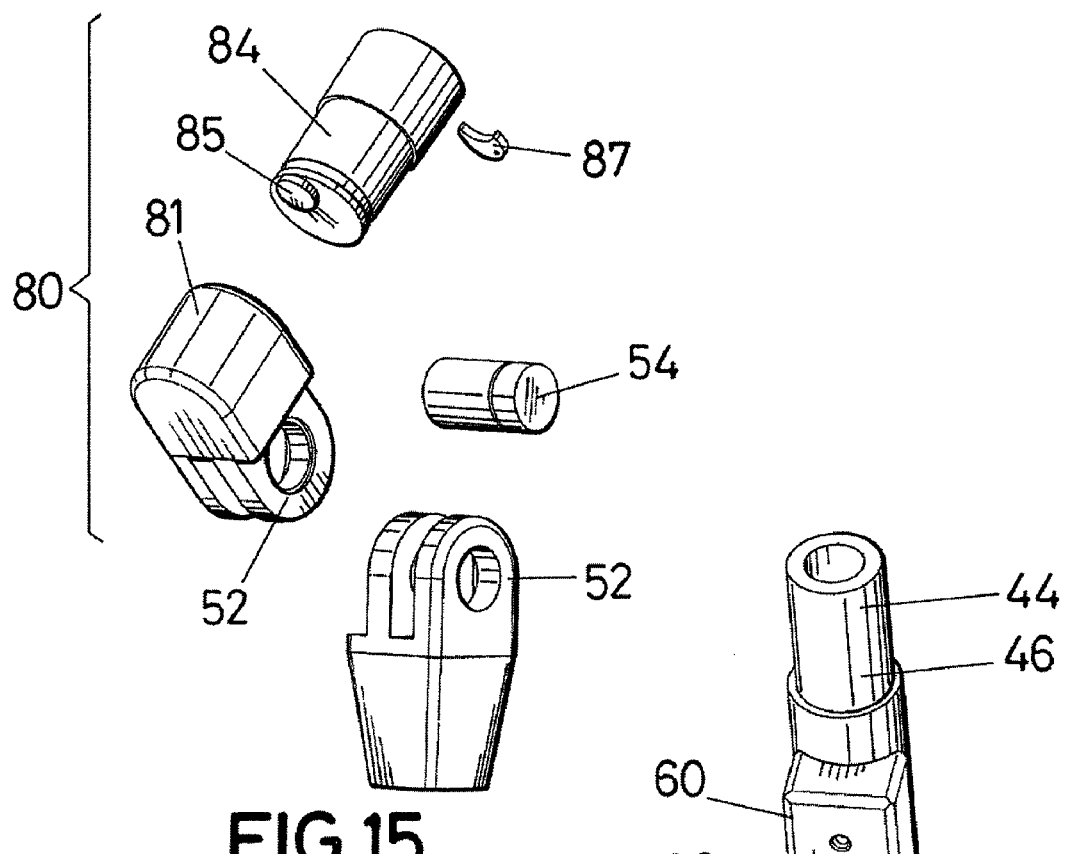
FIG. 15 shows a different exploded view of the elements in FIG. 13.
Figure 16:
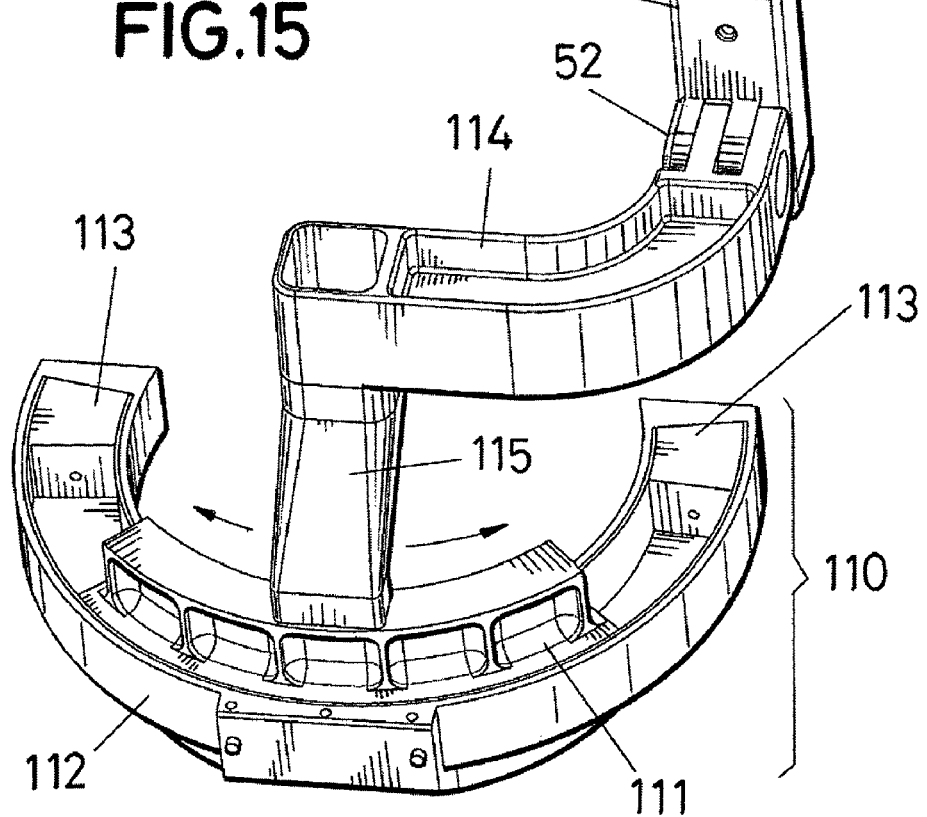
FIG. 16 shows a lower linkage assembly with an LRM, a joint, a derivation element and another ALM for coupling to the boot.
Figure 17:
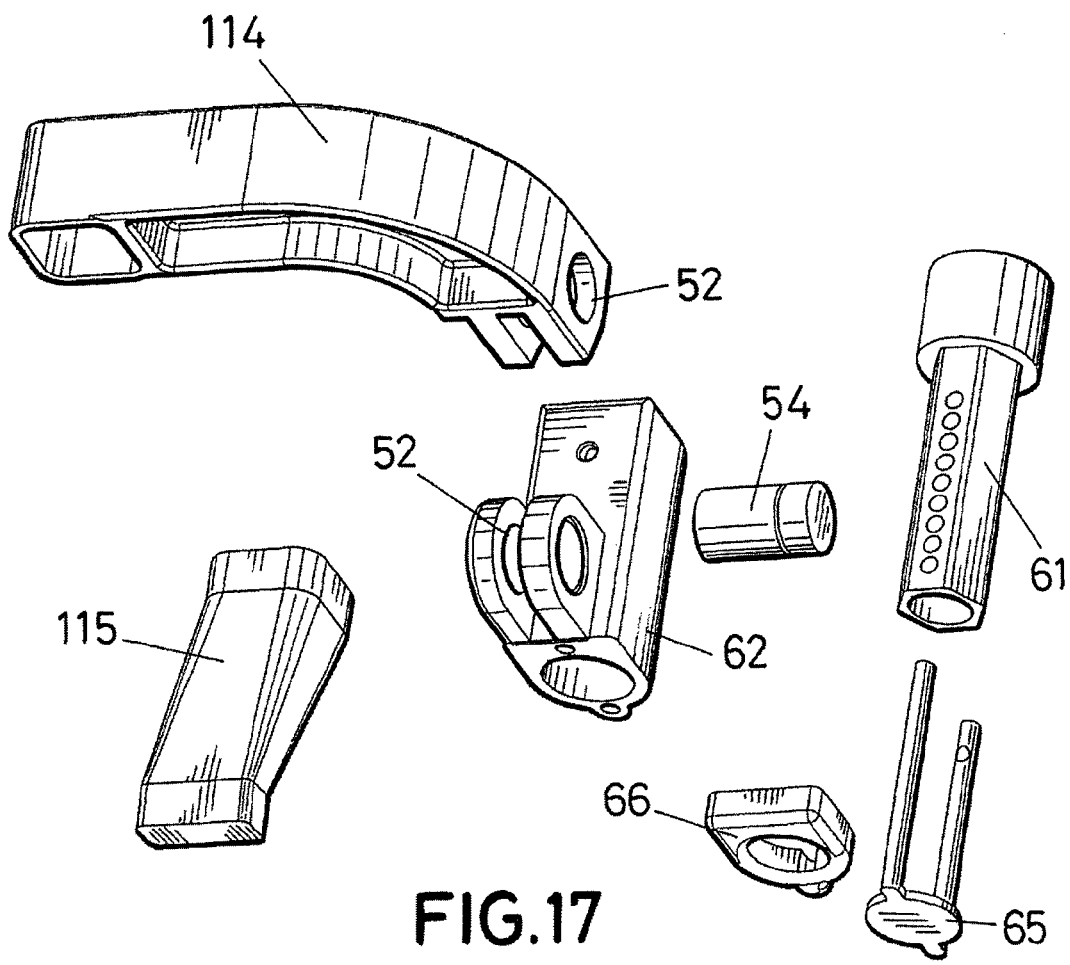
FIG. 17 shows an exploded view of the elements in FIG. 16 except for the ALM.
Figure 18:
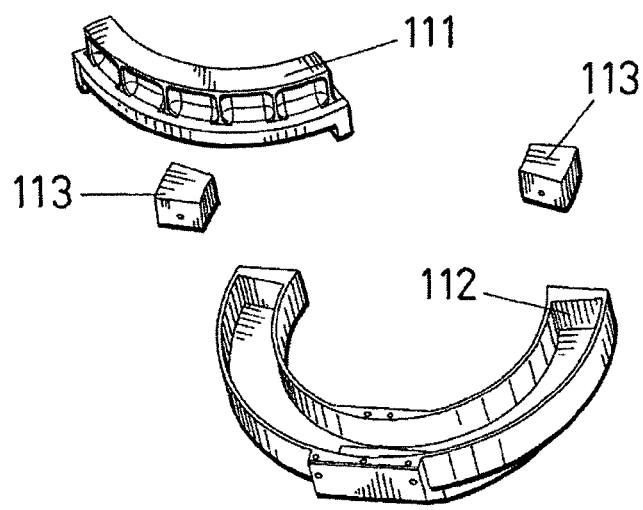
FIG. 18 shows an exploded view of the ALM of FIG. 16.

An alternative double hinge (53), shown in FIG. 2C, has its two axis turned 90 degrees in respect of the double hinge shown in FIG. 2 and FIG. 2B.

The upper linkage assembly (41) is linked at its lower end to the lower linkage assembly (44), preferably at the height of the knee and using a joint at the knee (2) preferably a hinge type joint (52) allowing the natural flexion and extension of the knee (3), but not its torsion.

It is possible to include at any point along the upper linkage assembly (41), between the LRM (60) and the knee, an angle limitation mechanism (ALM) (70, 80, 90) in a parallel axis to the longitudinal axis of the femur limiting rotation about the longitudinal axis as illustrated in FIGS. 14, 15, 24, 25 and 26 to 29. This ALM limits the rotation or relative torsion between the upper end (42) of the upper linkage assembly (41) and the lower end (43) of the upper linkage assembly (41) around an axis passing through the upper (42) and lower (43) ends of the upper linkage assembly (41).

The first embodiment discussed herein has two ALMs. The first ALM (80) connects the upper linkage assembly (41) to the lower linkage assembly (44) through itself and through the hinge (52) and its pin (54). The ALM shown in FIGS. 14 and 15 includes an outer member (81) or hub and an inner member (84) or shaft that rotate relative to each other within a limited range around the longitudinal axis of the upper linkage assembly. The inner member (84) has a raised element (85) on its surface and the outer member (81) has an internal surface (83) with a groove or guide path (82) on the same. The guide path is kidney-shaped. When the inner member (84) or shaft is introduced in the outer member (81) or hub, the raised element (85) can only move within the guide path (82) of the internal surface (83) of the outer member (81) or hub. Therefore, the rotation is limited by the length of the guide path (82). The length of the guide path (82) and therefore the rotation of one member (81, 84) relative to the other, can be reduced if limiting elements (87) or pins are introduced in holes (86) made on the guide path (82) surface.

After the ALM (80) and the hinge (52) is the lower linkage assembly (44) (see, e.g., FIGS. 2 and 16 to 18), which is coupled to a second length regulating mechanism or LRM (60) that allows the variation in length of the lower linkage assembly (44). This LRM (60) is joined to another hinge (52), for connecting the LRM (60) with a curved element (114) that extends the exoskeleton from the side of the leg or legs to the back part of the same. Next, a connection element (115) extends downward and is joined to a second ALM or boot ALM (110) shown in FIG. 18. This ALM (110) is mainly made up of an element with a semicircular groove or slide (112) and a curved slipping element or runner (111) introduced in the slide (112), so that the curved slipping element (111), fixed to the connection element (115) moves or slips between the two ends of the semicircular groove or slide (112). The element including the slide (112) is fixed to the rear part of the second support member or boot (31). The rotation of the slipping element or runner (111) can be limited with the inclusion in at least one end, and preferably both, of the semicircular groove or slide (112) of one stop element (113), and depending on the size of the stop elements (113) the rotation will be larger or smaller.

The hinge (52) placed in the second LMR (60) is used for absorbing the movements of the leg inside the boot (31), specifically the movements forwards and backwards of the leg.

Figure 24:
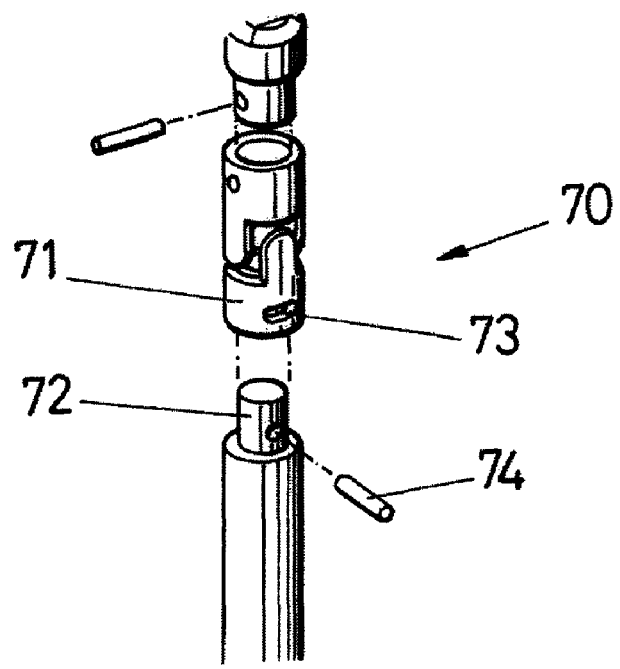
FIGS. 24 and 25 show another exemplary embodiment of an ALM.
Figure 25:
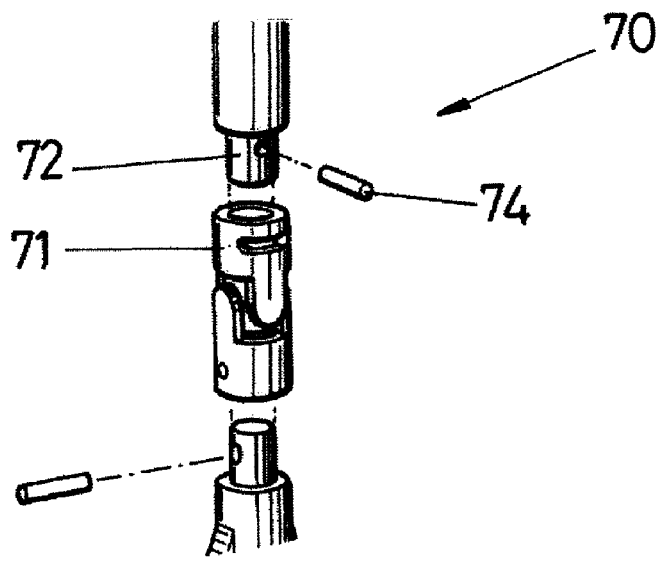
Figure 26:
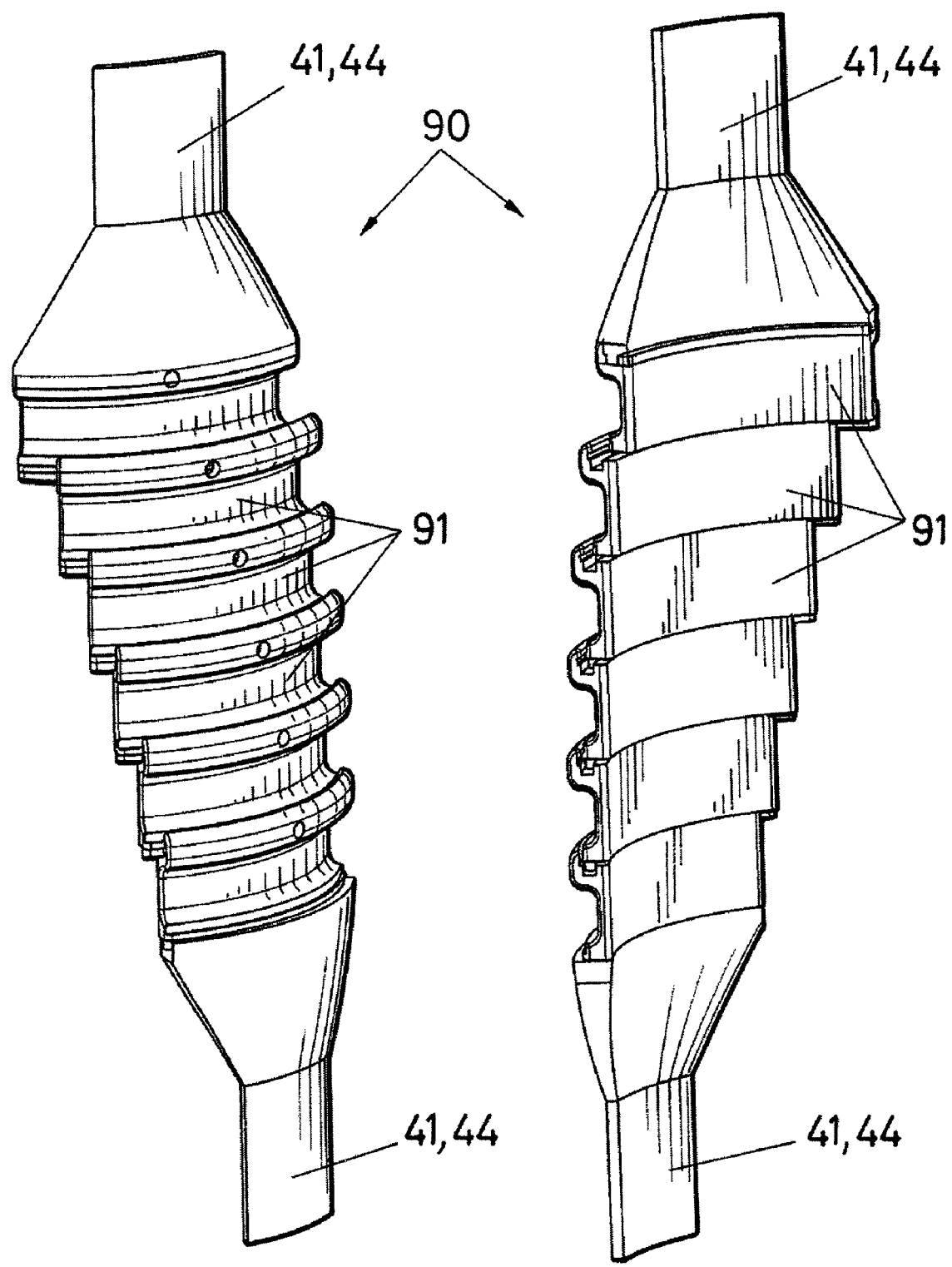
FIG. 26, 26b, 27, 28 and 29 show yet another embodiment of an ALM and its components.
Figure 26B:
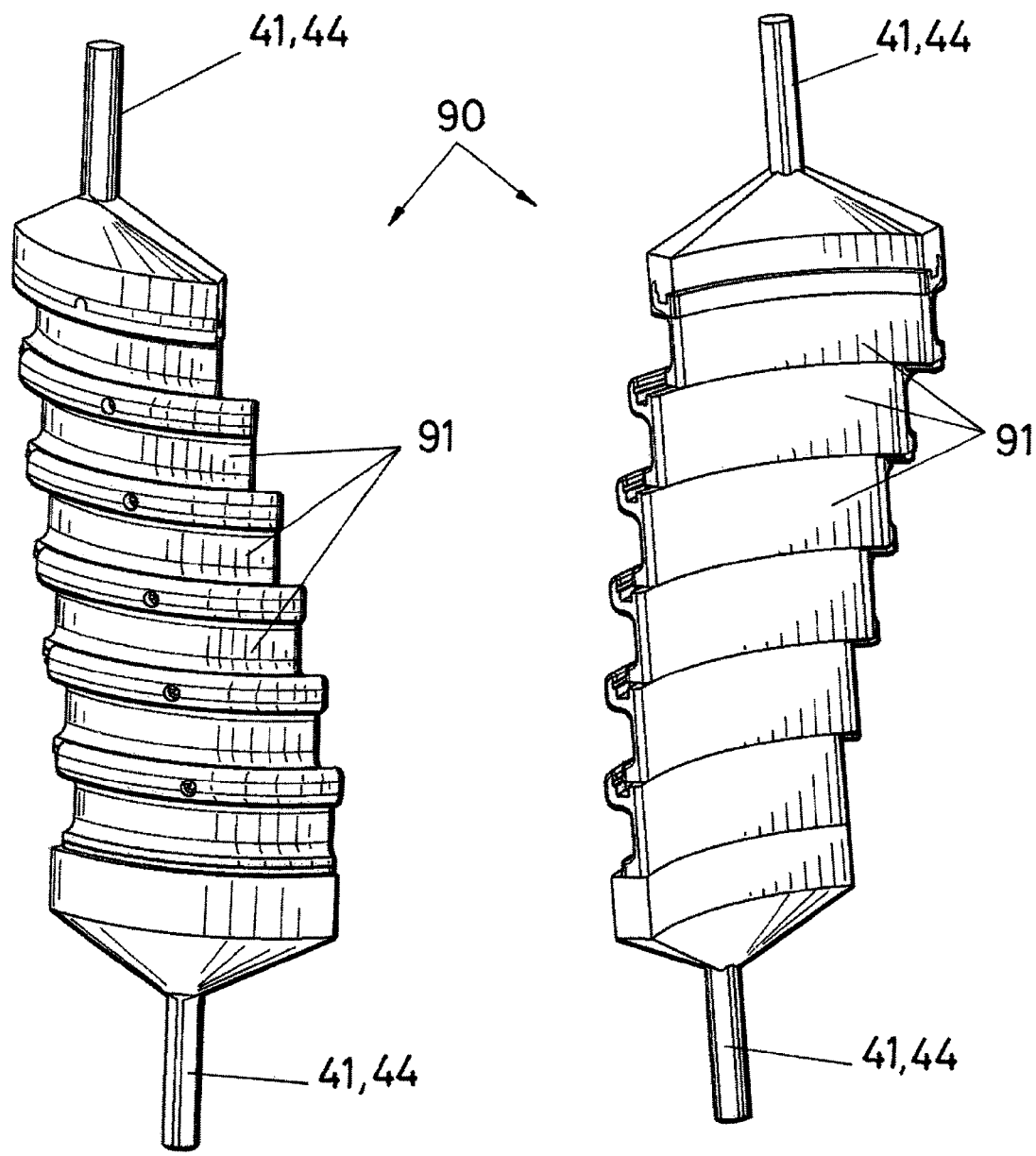
Figure 27:
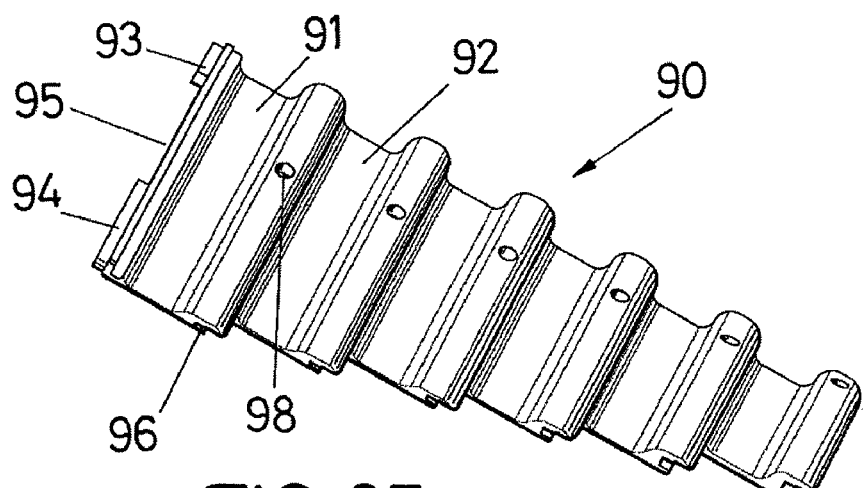
Figure 28:
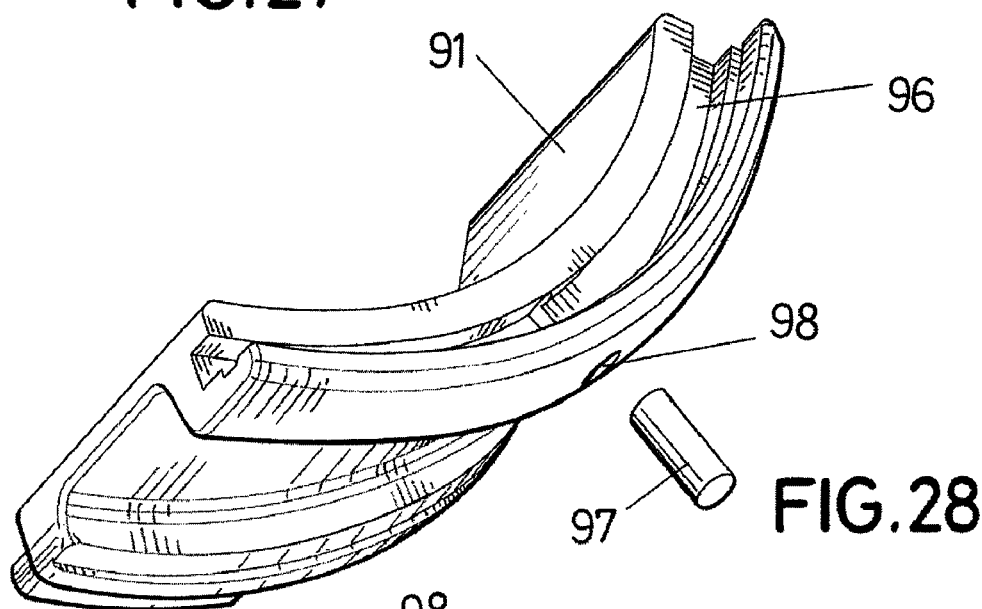
Figure 29:
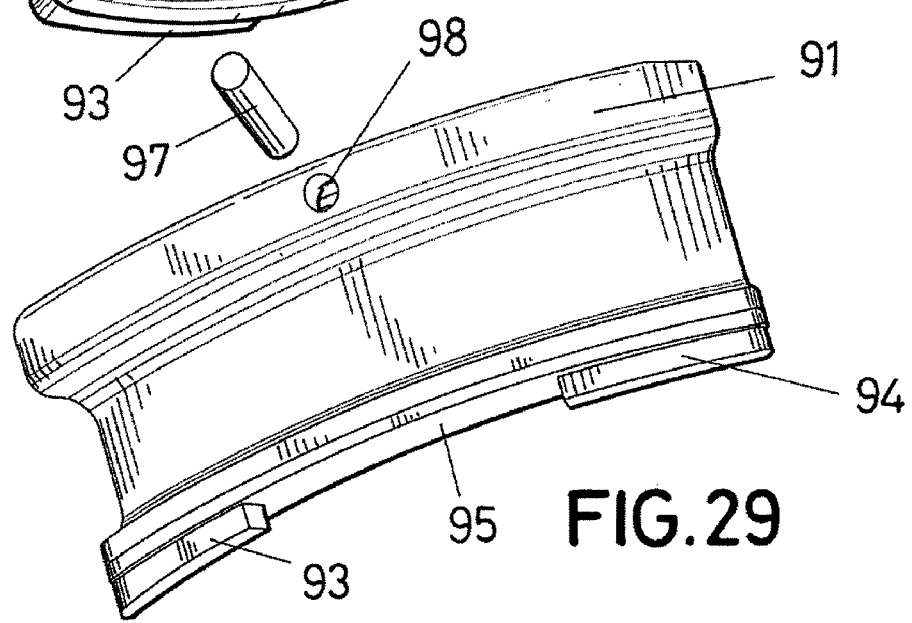

The ALM described before (80, 110), can be substituted for other alternative angle limitation mechanisms (70, 90). For example, a second embodiment of ALM (70) is illustrated in FIGS. 24 and 25. The ALM (70) has a shaft (72) and hub (71) system in which the hub (71) has a groove, slit or window (73) in its surface which is perpendicular to the longitudinal axis of rotation and the shaft (72), that is concentric with the hub (71), includes a lug (74) perpendicular to the longitudinal axis of rotation. The shaft (72) is introduced in the hub (71) and the lug (74) in the groove (73) such that the rotation of the shaft (72) with regard to the hub (71) is thus limited by the length of the groove (73), specifically when the lug (74) abut against one of the two ends of the groove (73). The ALM can be placed along the upper linkage assembly (41), and therefore the same is divided into two parts so that one part connects with the ALM shaft (72) and the other with the ALM hub (71).

Yet another alternative of a rotation limiting mechanism or angle limitation mechanism (ALM) (90), as illustrated in FIGS. 26 to 29, includes at least two partially curved plates (91, 92) overlapping one another. Each curved plate has two rails (93, 94) on its lower edge and a groove (96) on its upper edge, and both rails (93, 94) are separated between them by a gap or space (95). The spaced apart rails (93, 94) of the first curved plate (91) are introduced in the groove (96) of the second curved plate (92), therefore allowing a rotational movement of one plate relative to the other. In order to limit the rotational movement, a stop pin (97) can be introduced in a hole (98) that crosses the groove (96) of the second curved plate, so that the first curved plate can only move the length of the existing gap (95) between the rails (93, 94) of the first curved plate.

The previous ALM embodiments can be placed anywhere along the upper linkage assembly (41), between the hip (5) and knee (2), dividing in that way the upper linkage assembly into two parts so that one part of the upper linkage assembly (41) links with one part of the ALM (71, 80, 91) and the other part of the upper linkage assembly with the ALM lower element (72, 84, 92). In the same way the above ALM's can be placed anywhere in the lower linkage assembly.

The device can also have coupling systems (60), that are the same as the LRM or length regulation mechanism, as illustrated in FIGS. 9 to 12, allowing the connection and disconnection between two members or components of the device for the purpose of aiding the assembly or disassembly of the exoskeleton, as well as its use or arrangement on the skier or user thereof. The number of coupling systems (60) as well as the features of each of them can vary, the coupling systems (60) being able to be located at any point along the transmission chain forming the exoskeleton for the purpose of aiding in removing or releasing the exoskeleton. The coupling systems (60) are preferably located in the lower linkage assembly (44) between the second support member and the knee, since the exoskeleton can thus be disconnected from said second support member, for example, the boots (31) or the skis (1) or the bindings of the boot (31) to the ski (1). The coupling systems (60) are preferably quick coupling systems and can also be used as means of extending the length of the upper or lower linkage assembly, and therefore of the exoskeleton. The previously described LRM for extending the length of the linkage assemblies can also be used as a coupling mechanism (60).

As previously mentioned, both boots (31) and therefore both feet are linked by the previous alternatives through the hip, also causing the connection of both lower extremities (FIG. 2B).

Figure 20:
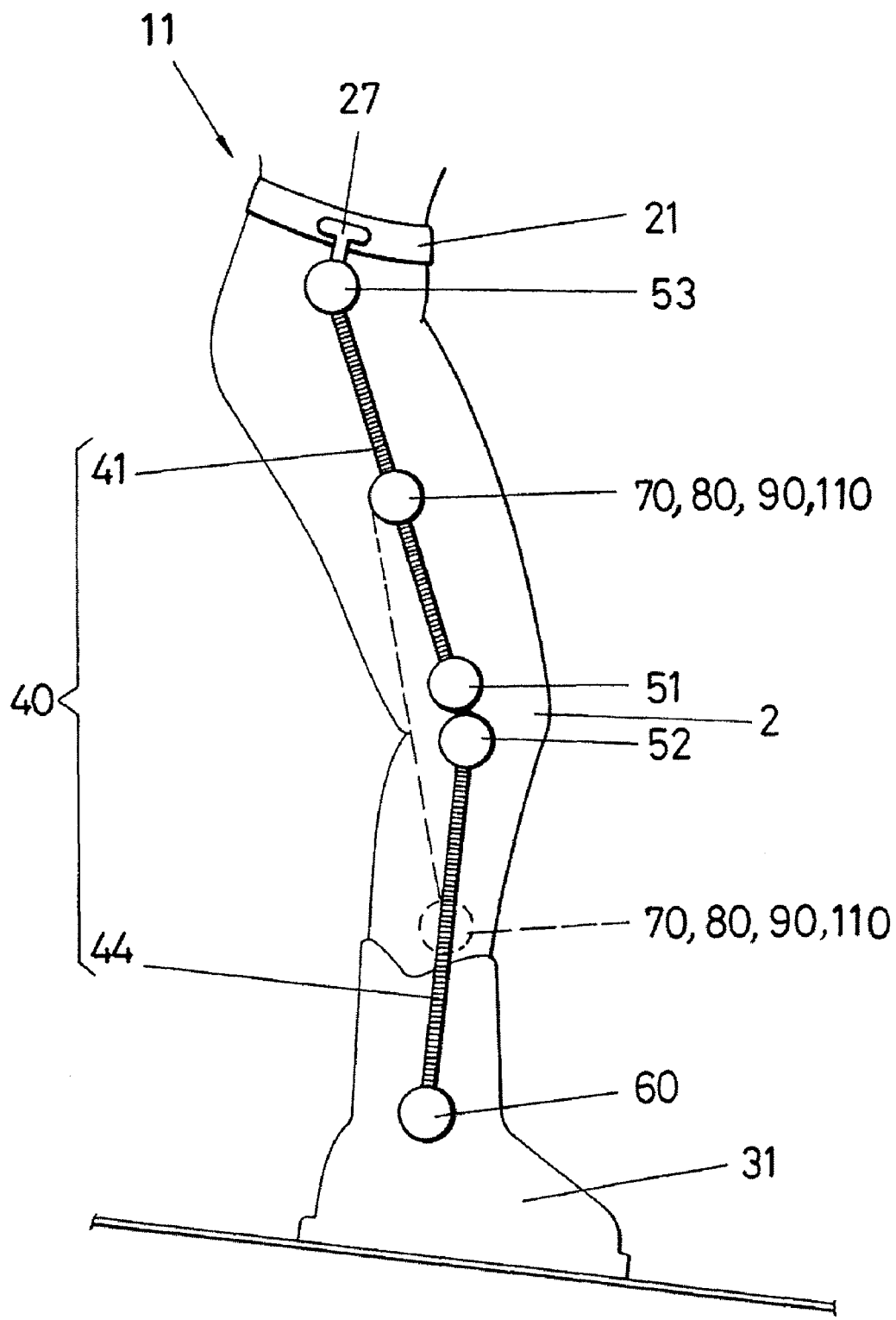
FIG. 20 shows a skier's lower extremity with a schematic depiction of a second exemplary embodiment of the invention.

A second embodiment (11), shown schematically in FIG. 20, has an exoskeleton that only includes one ALM (70, 80, 90, 110). The embodiment (11) shown includes the same elements as the previous embodiment (10) up to the artificial joint at the height of the knee. In this second embodiment (11), the artificial joint at the height of the knee is made up of a torque transmitting mechanism or joint (51) allowing angular misalignments between the two torque axis of the linkage assemblies (41, 44) or elements connected by the joint (51) and a hinge (52) that supports or anchors the ends of the linkage assemblies (41, 44) or elements connected by said transmission joint or mechanism. This transmission mechanism can be an elastic joint, a universal or Cardan joint (51), a cable type for odometers or any other similar joint that transmits the torque in the above-mentioned conditions, such that transmits torque between the torque axis of the two elements connected by the joint, allowing said transmission of the torque independently of the angular alignment between the torque axis of both elements.

After the artificial joint at the height of the knee, the lower linkage assembly (44) is connected to the previous artificial joint through its upper end (45), being the lower end (46) of the lower linkage assembly (44) linked to the second support member with a coupling or fixation member (60), preferably quick coupling or fixation members with the same components as the previously described LRM (60). The second support member can for example be the ski boots (31) or the binding of the boot to the ski or the ski (1) itself.

In this second embodiment (11), it is only required one ALM that can be placed in any place along the linkage assembly (40), that is to say, at the upper linkage assembly (41) or at the lower linkage assembly (44).

As illustrated in FIG. 20, the mentioned ALMs, can be located between the hip (5) and the knee (2) or between the knee (2) and the boot (31), at each of the skier's (3) lower extremities.

Figure 21:
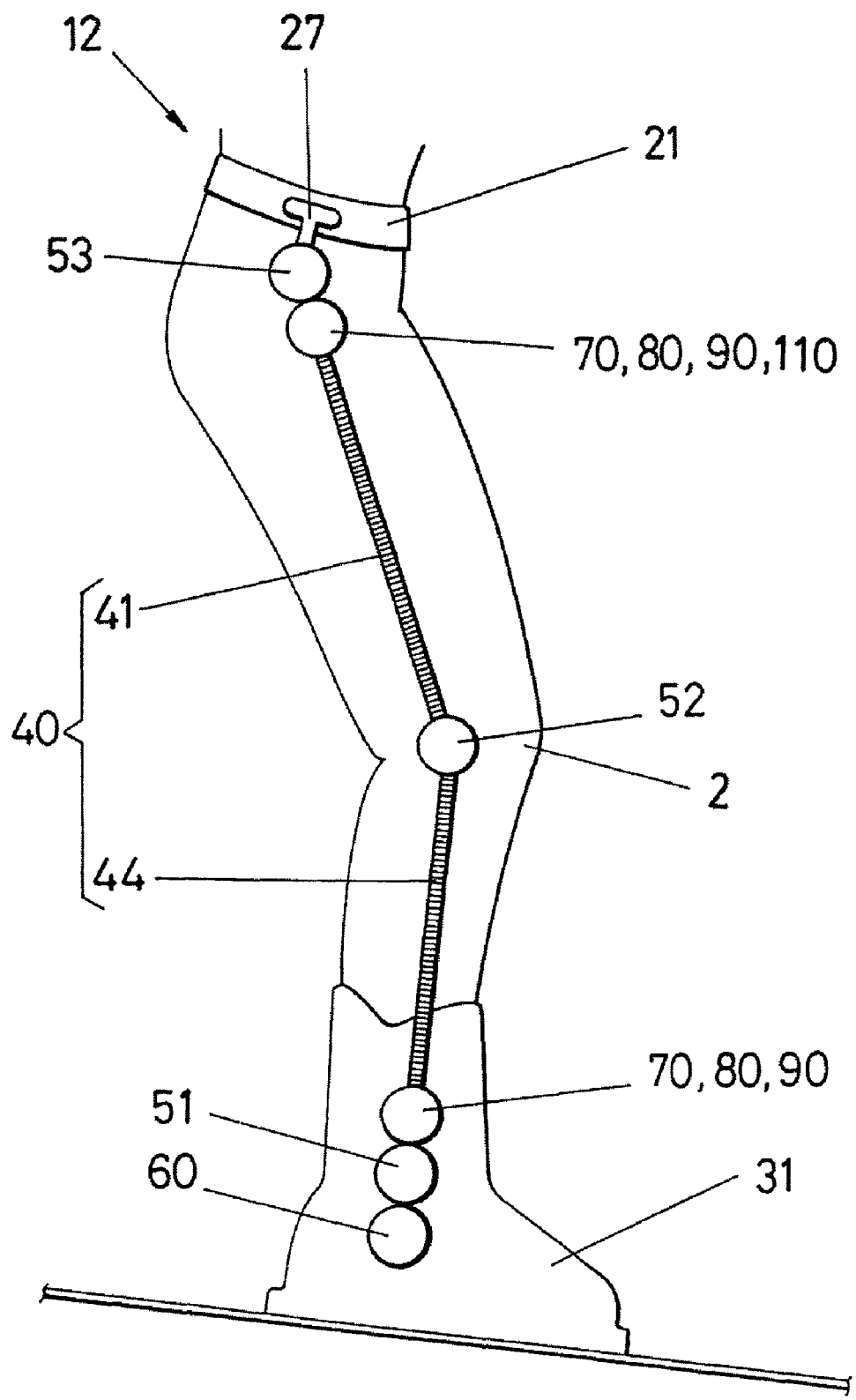
FIG. 21 shows a skier's lower extremity with a schematic depiction of a third exemplary embodiment of the invention.

FIG. 21 schematically illustrates a third preferred embodiment (12) similar to the previously described construction. In this third embodiment, a first support member (21) is located at the height of the hip or waist which, at its sides and for its linking with the upper linkage assembly (41), has a T element (27) and an artificial hinge joint (52) and after this, and at any point along the upper linkage assembly (41), it has an ALM (70, 80, 90, 110). At the lower end (43) of upper linkage assembly (41), at the height of the skier's knee, and as a linkage to the lower linkage assembly (44), a hinge-type joint (52) is used, allowing flexion and extension of the knee. Then the lower linkage assembly (44), coupled at its upper end (45) to the hinge joint (52) and at its lower end (46) to the side of the second support member, boot (31), binding of the boot to the ski or the ski itself, is arranged. Arranged along the lower linkage assembly (44) and preferably close to the linking between the lower linkage assembly (44) and the second support member, preferably in this embodiment the boot (31), there is another artificial joint (51) that transmits the torque between the respective torque axis of the elements connected by the joint, allowing said torque transmission regardless of the angular alignment between the respective torque axis, as well as another ALM (70, 80, 90).

Figure 22:
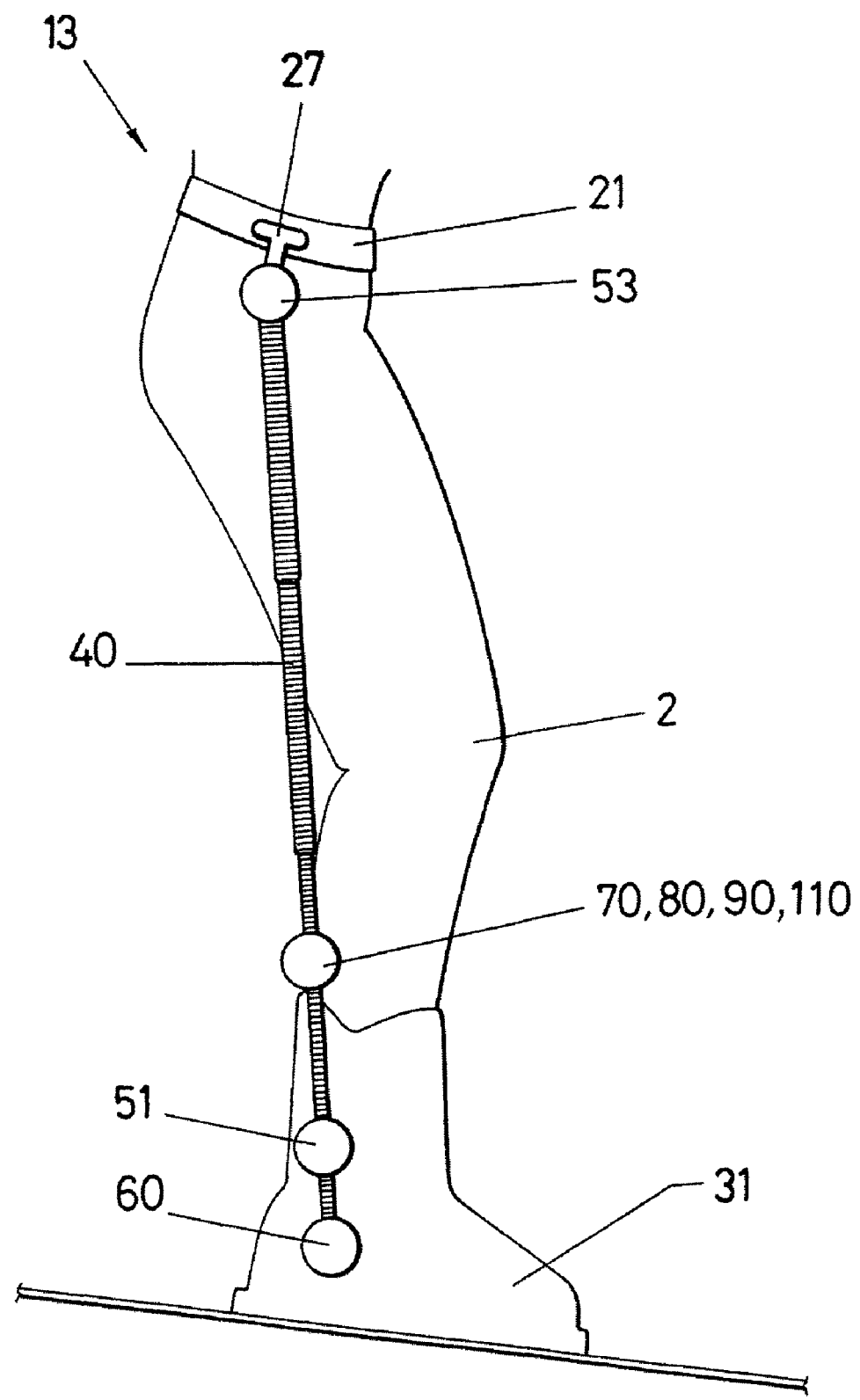
FIG. 22 shows a skier's lower extremity with a schematic depiction of a fourth exemplary embodiment of the invention.

In another preferred embodiment (13), schematically illustrated in FIG. 22, an extendible single linkage assembly (40) is located between the first support member (21) located above the knee, preferably at the height of the hip, and the second support member located below the knee, preferably at the boot (31). As in other embodiments, the exoskeleton also incorporates joints, preferably movement and torque transmission joints (51), such that transmits the torque between the respective torque axis of the elements connected by the joint, allowing said torque transmission regardless of the angular alignment between the respective torque axis, as well as an ALM (70, 80, 90, 110) at any point of the extendible linkage assembly located between the first support member and the second support member, preferably the belt (21) and the boot (31) respectively. This linkage assembly (40) is elongated or shortened automatically following the extension-flexion movements of the skier's leg, due to, for example, it telescopic condition.

The previously described preferred embodiments form protection by way of an exoskeleton attached to the individual at the waist, legs and feet, limiting relative rotation or torsion between the point of coupling to the body of the first support member and the point of coupling to the body of the second support member, preventing knee injuries in particular, and any bone injury in general, in the manner already described.

Figure 23:
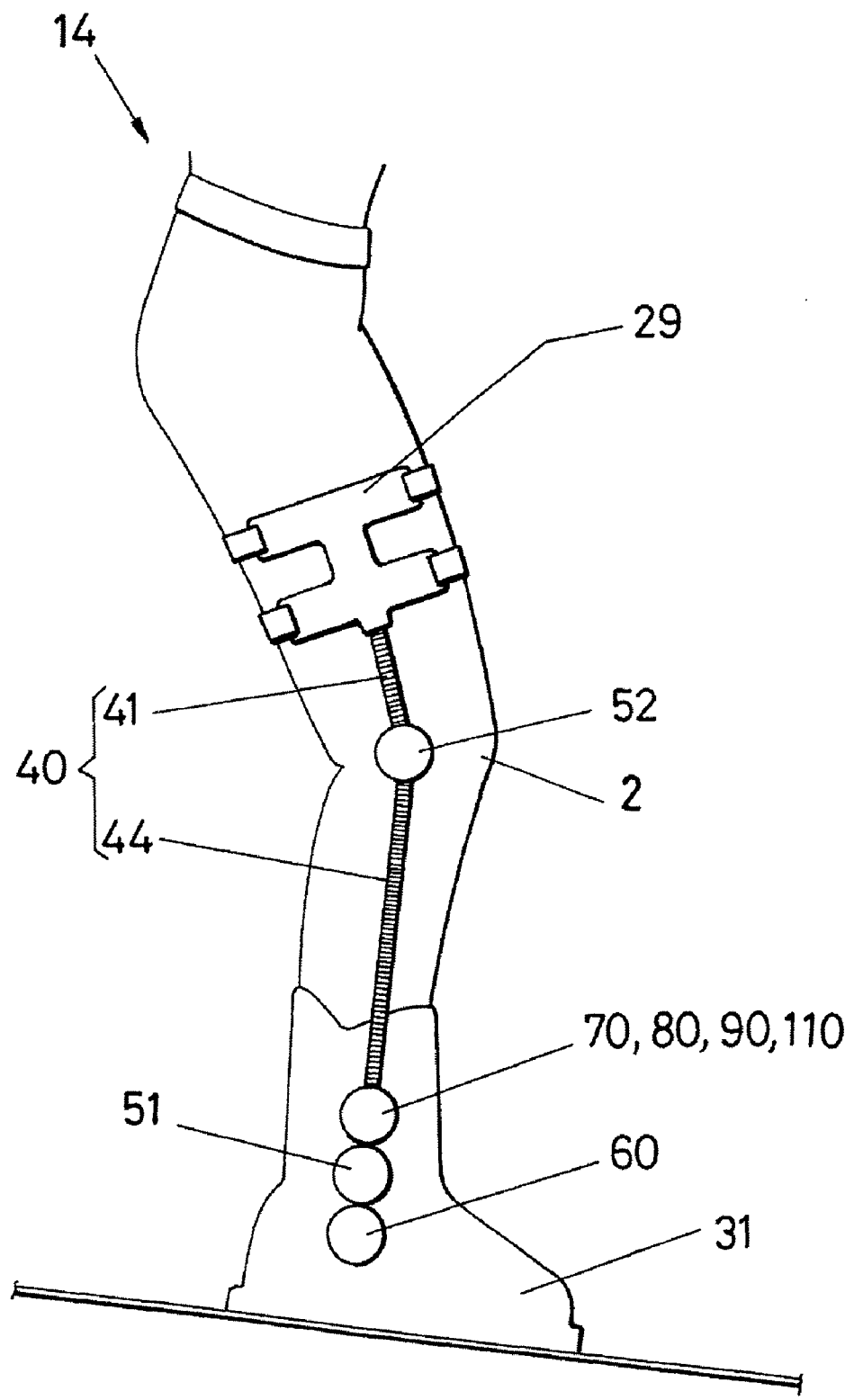
FIG. 23 shows a skier's lower extremity with a schematic depiction of a fifth exemplary embodiment of the invention.

In another preferred embodiment (14) illustrated schematically in FIG. 23 the first support member (21) located at the height of the skier's (3) hip (5) is replaced with a support member (29) located at the thigh (4), for either one or in both of the skier's (3) legs. In this construction, the first support member can be attached to the thigh by a clamp (29).

The remaining components, such as joints and limiting mechanisms, will be included in the exoskeleton in the same way and with the same alternatives as in the previous embodiments, with the obvious limitations due to the different constructive characteristics and mainly due to the inexistence in this latter embodiment of a coupling of the exoskeleton at the height of the hip (5). The upper and lower linkage assemblies (41, 44) can be fastened to different parts of the leg by mixed clamps (108) placed along both linkage assemblies (41, 44). These clamps (108) are preferably formed by a rigid part and a soft part, like a belt, used to fasten the rigid part to the leg. The upper and lower linkage assemblies (41, 44) can be replaced by ergonomic elements, that is to say elements that adapt to the body of the user.

It is possible to use ergonomic anatomical elements independent of the linkage assemblies, such as plates made of a rigid and lightweight material placed between the leg and linkage assemblies to protect or isolate the leg from the movement thereof, making the use of the exoskeleton more comfortable. The foregoing is particularly useful when the exoskeleton is introduced or inserted in ski pants or a cover made of a flexible material and close to the cushioning in the areas where friction with the body occurs, and the device will neither be visible or uncomfortable while practicing skiing.

As previously mentioned in the first embodiment, it is possible to replace the upper linkage assembly (41) and the lower linkage assembly (44) of any of the different preferred embodiments with extendible members or linkages in order to thus adapt them to the specific measurements of each user. In the described case of a single extendible linkage assembly (100), as shown in FIG. 22, this is adaptable due to its own nature. The adaptation to the specific measurements of the skier or user can be done by the previously described LRM (60).

Figures 30, 31:
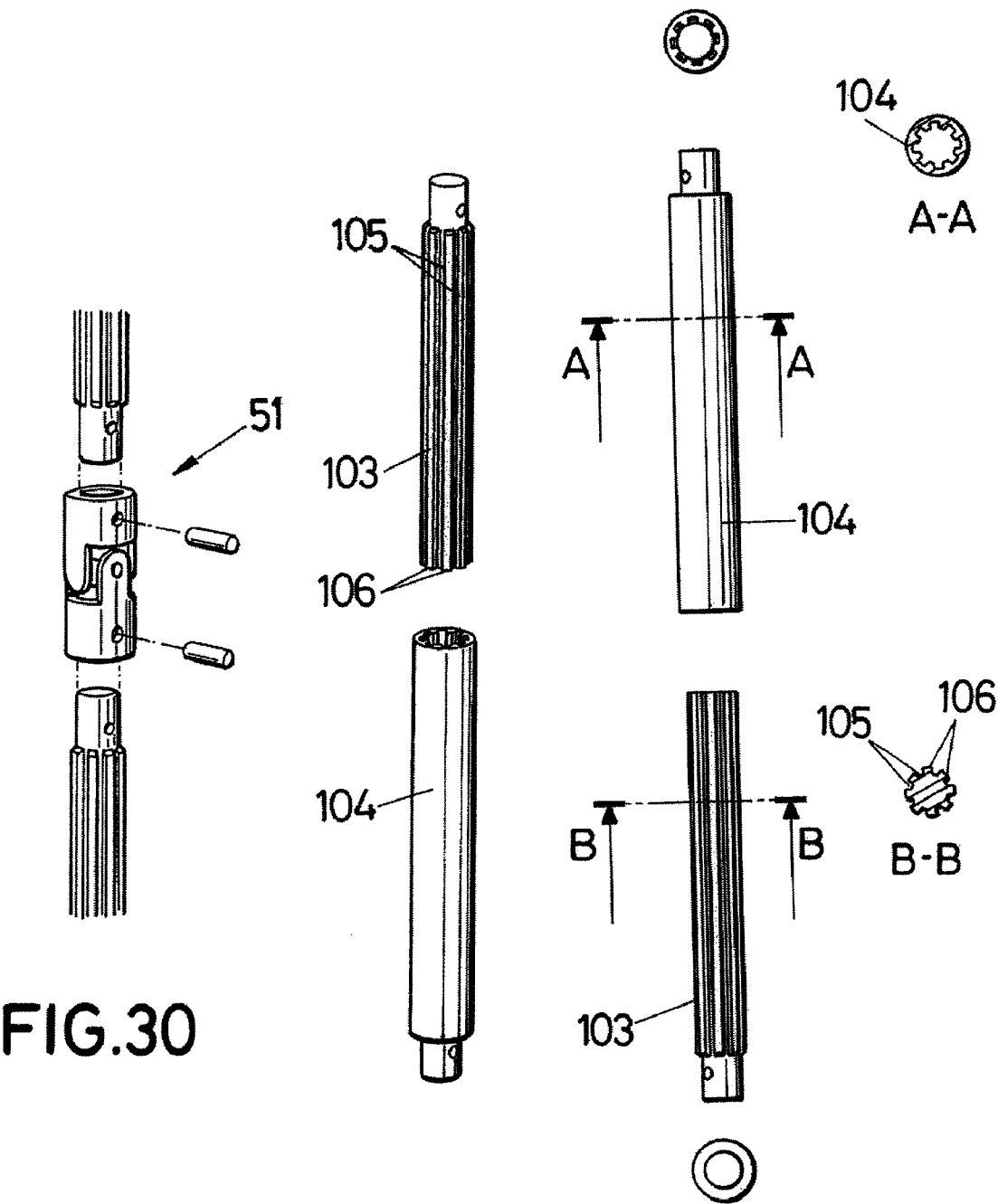
FIG. 30 shows an example of a universal or Cardan joint.
FIG. 31 shows an embodiment of an extendible linkage assembly.
Figure 32:
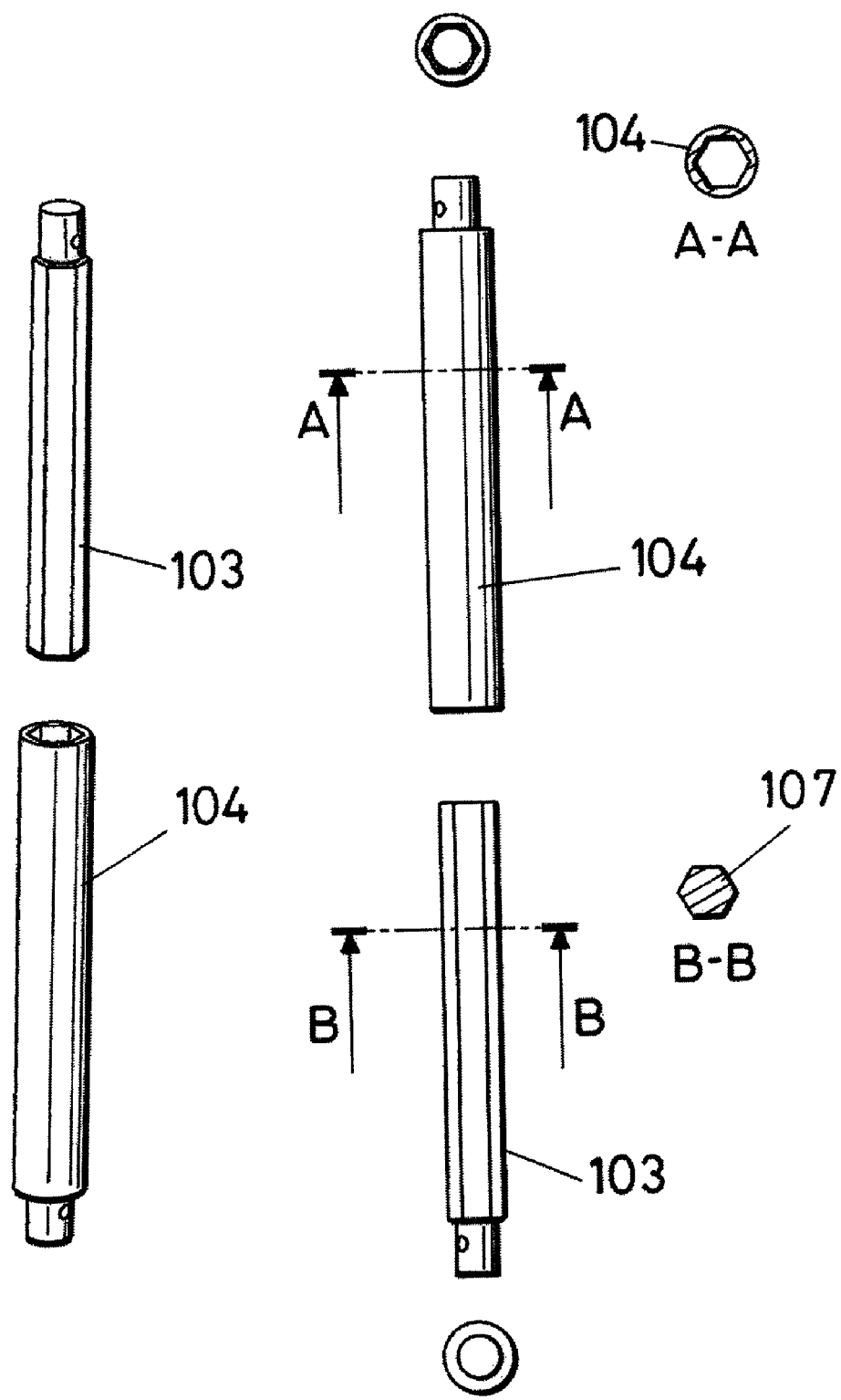
FIG. 32 shows another embodiment of an extendible linkage assembly.

Another way of achieving the extension of the linkage assembly (40) or of the upper and lower linkage assemblies (41, 42) is by a telescopic member, that is to say, the former can be formed by two members, an outer sheath (104) and an inner guide (103), which longitudinally slide with respect to one another as illustrated in FIG. 31. The guide (103) preferably has a circular section defining longitudinal projections (106) and grooves (105) coupled inside the sheath (104) that has a complementary section. This coupling allows carrying out an extendible linkage and, by way of the projections (106) and grooves (105), transmitting the torque in an optimal manner between the guide and the sheath. It is also possible to use other configurations which allow adjusting the linkage to the measurements of each user. It is also possible to use instead of projections (106) and grooves (105) a hexagonal-shaped (107) inner guide and a outer sheath in the extendible linkage as shown in FIG. 32.

In summary, a device of this type on either side of the hip allows, as previously described, limiting the relative rotation or torsion between the point of coupling to the body of the first support member and the point of coupling to the body of the second support member.

As well, due to its constructive features, this device limits the potential dangerous movements of the lower extremities of the user in all axis, while it allows the necessary movements for ski practice and other activities, setting up a protection against injuries that the practicing activity could produce.

The different components of the safety and control device object of the present invention can be made of different materials, either metals, alloys, or fibers, but they must be materials that can resist the stress to which the device is subjected.

The invention claimed is:
1. An exoskeleton to be worn by a person to provide protection against injuries, comprising:
   at least one first support member configured to couple the exoskeleton to the person's body above the knee;
   at least one second support member configured to couple the exoskeleton to the person's body below the knee;

a linkage assembly comprising an upper end and a lower end, the linkage assembly coupled at the upper end of the linkage assembly to the first support member and coupled at the lower end of the linkage assembly to the second support member, the linkage assembly extending generally along the leg when the exoskeleton is worn by the person; and at least one angle limitation mechanism that limits the relative torsion between the coupling to the body of the first support member and the coupling to the body of the second support member.

2. The exoskeleton according to claim 1, wherein the at least one angle limitation mechanism limits the relative torsion between the coupling to the body of the first support member and the coupling to the body of the second support member so as to prevent relative torsion outside a predetermined rotational range while permitting a free unrestricted relative torsion within the predetermined rotational range.

3. The exoskeleton according to claim 1, further comprising at least one joint between two elements of the exoskeleton such that the at least one joint transmits torque between the two elements, allowing said torque transmission independently of angular alignment between the respective torque axis of the two elements connected between them by said joint.

4. The exoskeleton according to claim 1, wherein the linkage assembly comprises an upper linkage assembly with a respective upper end and a lower end, and a lower linkage assembly with a respective upper end and a lower end, and wherein, when the exoskeleton is worn by the person, the upper linkage assembly extends from the first support member to about the person's knee, and the lower linkage assembly extends from about the person's knee to the second support member.

5. The exoskeleton according to claim 4, wherein the lower end of the upper linkage assembly is linked to the upper end of the lower linkage assembly by an artificial joint located at about the height of the person's knee, and said joint allowing a flexion-extension movement of the knee.

6. The exoskeleton according to claim 5, wherein the joint is a hinge.

7. The exoskeleton according to claim 5, wherein the joint transmits the torque between the upper linkage assembly and the lower linkage assembly, said joint allowing torque transmission independently of the angular alignment between the torque axis of the upper and lower linkage assemblies connected between them by said joint.

8. The exoskeleton according to claim 7, wherein the joint includes a hinge.

9. The exoskeleton according to claim 1, wherein the first support member is configured to couple the exoskeleton to the person's body at the waist or hip.

10. The exoskeleton according to claim 1, wherein the first support member is configured to couple the exoskeleton to the person's thigh.

11. The exoskeleton according to claim 5, wherein the angle limitation mechanism is located on the exoskeleton between the artificial joint at the height of the knee and the first support member.

12. The exoskeleton according to claim 5, wherein the angle limitation mechanism is located on the exoskeleton between the artificial joint at the height of the knee and the second support member.

13. The exoskeleton according to claim 4, comprising two angle limitation mechanisms, one located between the artificial joint at the height of the knee and the first support member and the second one located between the artificial joint at the height of the knee and the second support member.

14. The exoskeleton according to claim 3, wherein the joint links the first support member with the linkage assembly.

15. The exoskeleton, according to claim 14, wherein the joint limits the movement or rotation in the sagital and transverse axis of the coxo-femoral joint, thereby limiting the flexion, the extension, the abduction and adduction of the leg to the natural ranges.

16. The exoskeleton, according to claim 15, in which the ranges of rotation allowed by the joint in the sagittal and transverse axis are adjustable.

17. The exoskeleton according to claim 16, further comprising a double hinge joint that joins the first support member to the linkage assembly, said double hinge joint allowing the flexion or articulation of the exoskeleton about two different axes.

18. The exoskeleton according to claim 1, wherein the lower end of the linkage assembly is linked to the second support member through a quick coupling mechanism that allows the person to quickly connect and disconnect the second support member to and from the linkage assembly.

19. The exoskeleton according to claim 1, further comprising one or more quick coupling mechanisms that allows the person to quickly connect and disconnect between them two parts of the exoskeleton.

20. The exoskeleton according to claim 1, wherein the angle limitation mechanism comprises a hub comprising a groove and a shaft that rotates within the hub and a lug, the lug movable inside the groove such that the ends of the groove limit the amount of relative rotation between the shaft and the hub.

21. The exoskeleton, according to claim 20, wherein the angle limitation mechanism comprises adjustable elements for changing the rotation range of one element relative to the other, both elements being placed in the groove or on the lug.

22. The exoskeleton according to claim 1, wherein the angle limitation mechanism comprises at least two partially curved plates overlapping one another and linked by rails allowing the two curved plates to slide relative to each other.

23. The exoskeleton according to claim 22, wherein the curved plates comprise adjustable stops that limit the amount by which the plates slide relative to each other.

24. The exoskeleton according to claim 1, wherein the angle limitation mechanism comprises an outer member or hub comprising an internal surface defining a guide path and an inner member or shaft comprising a raised rotational element disposed in the guide path so that rotation of the inner member is limited by the movement of the raised rotational element in the guide path.

25. The exoskeleton, according to claim 24, wherein the angle limitation mechanism comprises at least one limiting element introduced in at least one hole made in the guide path surface to adjust the length of the guide path and thereby the rotation of one member relative to the other.

26. The exoskeleton according to claim 1, wherein the angle limitation mechanism comprises an element with a semicircular groove and a curved slipping element or runner introduced in the groove so that displacement of the curved slipping element inside the groove is limited by the ends of the groove.

27. The exoskeleton according to claim 26, wherein the angle limitation mechanism is coupled to the linkage assembly through a curved element joined to a joint, extending said curved element from the side of the leg to the back part of the leg and connecting to the curved slipping element or runner through a connecting element.

28. The exoskeleton, according to claim 26, wherein the angle limitation mechanism comprises stop elements placed inside the semicircular groove in at least one end to adjust the rotation of the slipping element.

29. The exoskeleton according to claim 26, wherein the semicircular groove element is fixed to the second support member.

30. The exoskeleton according to claim 1, wherein the linkage assembly is extendable so as to be elongated or shortened to adapt to the size of a person's leg.

31. The exoskeleton according to claim 30, wherein the linkage assembly comprises a length regulating mechanism that makes the linkage assembly extendable, the mechanism comprising an inner member comprising a plurality of holes and an outer member comprising at least one sphere that is selectively insertable in one of the holes so as to adjust the relative position of the inner member and the outer member by pushing a pressing device that unblocks the spheres from the holes and releases the movement of the inner member in respect of the outer member.

32. The exoskeleton according to claim 30, wherein the linkage assembly comprises telescopic members.

33. The exoskeleton according to claim 1, comprising
at least one second support member for each leg,
at least one linkage assembly for each leg, and
at least one angle limitation mechanism for each leg.

34. The exoskeleton according to claim 3, wherein the joint is a universal or Cardan joint.

35. The exoskeleton according to claim 3, wherein the joint is an elastic joint.

36. The exoskeleton according to claim 1, wherein the second support member is a boot.

37. The exoskeleton according to claim 1, wherein the second support member is a ski.

38. The exoskeleton according to claim 1, wherein the second support member is the binding of the boot to the ski.

39. The exoskeleton according to claim 2, wherein the predetermined rotational range is adjustable by the person wearing the exoskeleton.

40. The exoskeleton according to claim 4, wherein the first support member is a rigid element.

41. The exoskeleton according to claim 40, wherein the first support member is a belt.

42. The exoskeleton according to claim 41, wherein the belt comprises two parts, a surrounding part and a front part, linked together to form a rigid whole by belt connections that are placed on the free ends of the surrounding part and the front part, so that said belt connections are superposed one on top of the other to form one element, and are fixed by a belt closure.

43. An exoskeleton to be worn by a person to provide protection against injuries, comprising:
at least one first support member configured to couple the exoskeleton to the person's body above the knee;
at least one second support member configured to couple the exoskeleton to the person's body below the knee;
a linkage assembly comprising an upper end and a lower end, the linkage assembly coupled at the upper end of the linkage assembly to the first support member and coupled at the lower end of the linkage assembly to the second support member, the linkage assembly extending generally along the leg when the exoskeleton is worn by the person; and
means for limiting the relative torsion between the coupling to the body of the first support member and the coupling to the body of the second support member.

* * * * *